(12) United States Patent
Rao et al.

(10) Patent No.: US 11,485,991 B2
(45) Date of Patent: Nov. 1, 2022

(54) MULTIFUNCTIONAL RECOMBINANT NUCLEOTIDE DEPENDENT GLYCOSYLTRANSFERASE PROTEIN AND ITS METHOD OF GLYCOSYLATION THEREOF

(71) Applicant: Council of Scientific & Industrial Research, New Delhi (IN)

(72) Inventors: Alka Rao, Chandigarh (IN); Rupa Nagar, Chandigarh (IN)

(73) Assignee: Council of Scientific & Industrial Research, New Delhi (IN)

( * ) Notice: Subject to any disclaimer, the term of this patent is extended or adjusted under 35 U.S.C. 154(b) by 609 days.

(21) Appl. No.: 16/091,186

(22) PCT Filed: Mar. 30, 2017

(86) PCT No.: PCT/IN2017/050116
§ 371 (c)(1),
(2) Date: Oct. 4, 2018

(87) PCT Pub. No.: WO2017/175239
PCT Pub. Date: Oct. 12, 2017

(65) Prior Publication Data
US 2021/0071221 A1    Mar. 11, 2021

(30) Foreign Application Priority Data
Apr. 5, 2016   (IN) .............................. 201611011974

(51) Int. Cl.
*C12P 19/00*   (2006.01)
*C12P 21/00*   (2006.01)
*C12N 9/10*    (2006.01)
*C12N 15/10*   (2006.01)

(52) U.S. Cl.
CPC .......... *C12P 21/005* (2013.01); *C12N 9/1051* (2013.01); *C12N 15/1003* (2013.01)

(58) Field of Classification Search
CPC .......................... C12N 15/1003; C12N 9/1051; C12N 9/1048; C12P 21/005
USPC ................ 435/97, 193, 252.3, 200
See application file for complete search history.

(56) References Cited

U.S. PATENT DOCUMENTS

| | | |
|---|---|---|
| 5,641,668 A | 6/1997 | Berger et al. |
| 6,379,933 B1 | 4/2002 | Johnson et al. |
| 6,743,606 B1 | 6/2004 | Wolter et al. |
| 7,338,933 B2 | 3/2008 | DeFrees et al. |
| 8,257,949 B2 | 9/2012 | Wakarchuk et al. |
| 8,895,014 B2 | 11/2014 | Fernandez et al. |
| 2014/0033369 A1 | 1/2014 | Tanaka et al. |

FOREIGN PATENT DOCUMENTS

| | | |
|---|---|---|
| CN | 102389030 A | 3/2012 |
| EP | 1981977 A4 | 4/2010 |
| EP | 2049144 B1 | 7/2014 |
| EP | 2049144 B8 | 2/2015 |
| WO | 0017226 A1 | 3/2000 |
| WO | 0200851 A2 | 1/2002 |
| WO | 2004009793 A2 | 1/2004 |
| WO | 2008151258 A2 | 12/2008 |
| WO | 2008151258 A3 | 2/2009 |
| WO | 2011073438 A3 | 8/2012 |
| WO | 2013088194 A1 | 6/2013 |

OTHER PUBLICATIONS

International Search Report and Written Opinion dated Sep. 25, 2017 in PCT/IN2017/050116 filed Mar. 30, 2017 (11 pages).
Rupa Nagar and Alka Rao, "An iterative glycosyltransferase EntS catalyzes transfer and extension of O- and S-linked monosaccharide in enterocin 96", Glycobiology, vol. 27, No. 8, pp. 766-776, (2017).
Sola, R.J., and Griebenow, Effects of Glycosylation on the Stability of Protein Pharmaceuticals, J. Pharm. Sci. vol. 98, No. 4, pp. 1223-1245, K. (Apr. 2009).
Sola, R.J., and Griebenow, K., Glycosylation of Therapeutic Proteins: An Effective Strategy to Optimize Efficacy. BioDrugs 24, 9-21 (2010).
Shental-Bechor, D. and Levy, Y., Effect of glycosylation on protein folding: A close look at thermodynamic stabilization, Proc. National I Academy of Sciences of the USA 105, 8256-8261, (2008).
Vasudevan, D., and Haltiwanger, R.S., Novel roles for O-linked glycans in protein folding, Glycoconjugate Journal 31, pp. 417-426 (Oct. 2014).
Hanson, S., Best, M., Bryan, M.C., and Wong, C.H., Chemoenzymatic synthesis of oligosaccharides and glycoproteins, Trends in Biochemical Sciences vol. 29, No. 12, pp. 656-663 (Dec. 2014).
Katayama, H., Asahina, Y., and Hojo, H., Chemical synthesis of the S-linked glycopeptide, sublancin, Journal of Peptide Science: an official publication of the European Peptide Society 17, pp. 818-821 (2011).
Zhang, Y. et al., Enhanced Epimerization of Glycosylated Amino Acids During Solid-Phase Peptide Synthesis, Journal of the American Chemical Society 134, pp. 6316-6325 (Mar. 2012).
Lindhout, et al., Site-specific enzymatic polysialylation of therapeutic proteins using bacterial enzymes, Proc. National Academy of Sciences of the USA 108, pp. 7397-7402 (May 2011).
Brimble, et al., "Synthesis of The Anti-Microbial S-Linked Glycopeptide, Glycocin F," Chemistry A European Journal Communication, DOI: 10.1002/chem.201405692, pp. 3556-3561 (2015).

(Continued)

*Primary Examiner* — Robert B Mondesi
*Assistant Examiner* — Mohammad Y Meah
(74) *Attorney, Agent, or Firm* — Dinsmore and Shohl

(57) ABSTRACT

The present invention generally relates to a method of peptides' or polypeptides' modification by glycosylation. In particular, the invention relates to one pot synthesis of disaccharide glycan on to the acceptor substrate and thereby generating O- and/or S-glycosylated neo-glycopeptides including antimicrobial peptides by using multifunctional recombinant nucleotide dependent glycosyltransferase.

12 Claims, 4 Drawing Sheets

Figure 1:
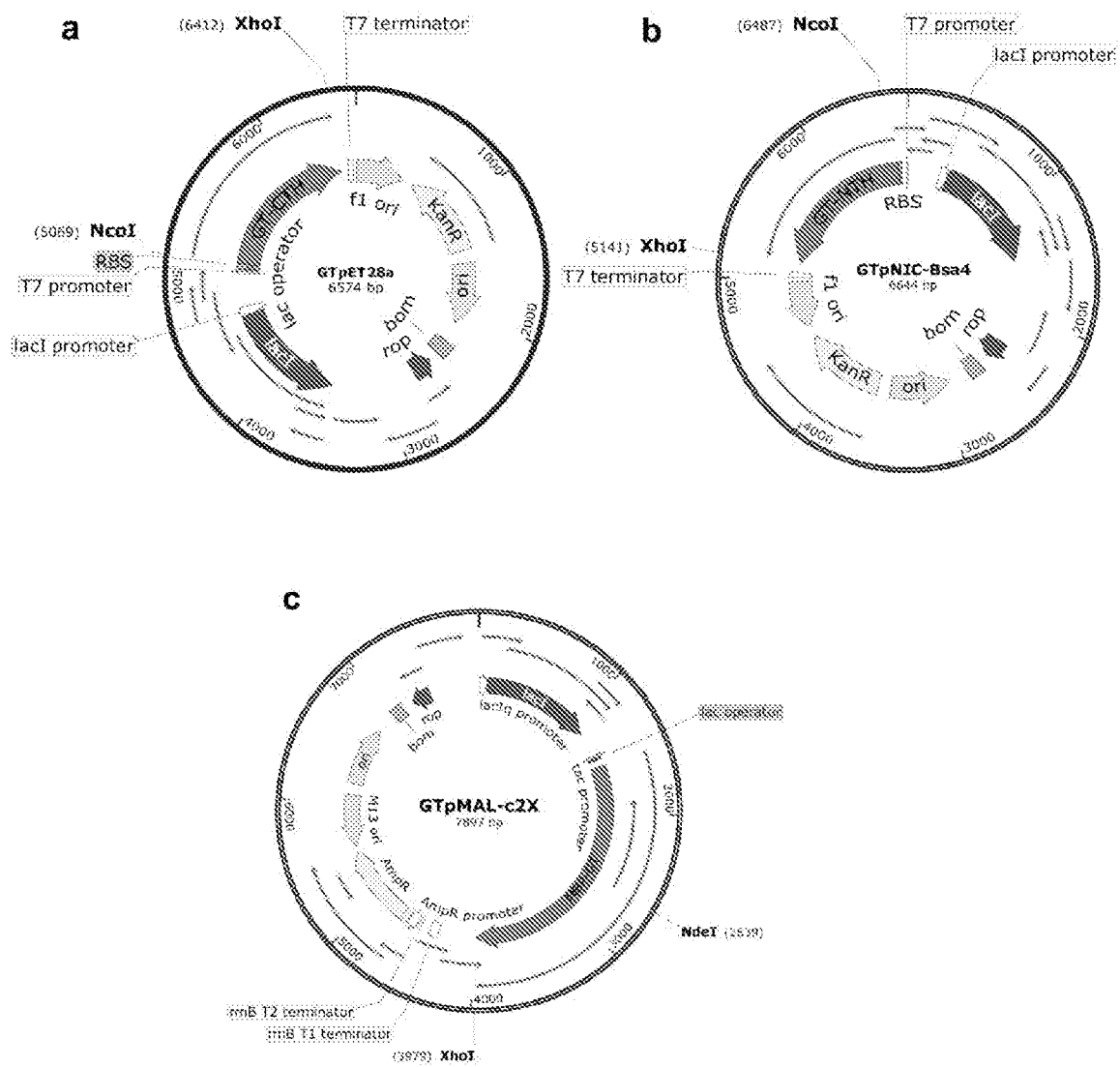

Specification includes a Sequence Listing.

(56) References Cited

OTHER PUBLICATIONS

Stepper, et al., Cysteine S-glycosylation, a new post-translational modification found in glycopeptide bacteriocins. FEBS Letters 585, pp. 645-650, (2011).
Kerr, A.P., The Bacteriostatic Spectrum and Inhibitory Mechanism of Glycocin F, a Bacteriocin from Lactobacillus plantarum KW30, A thesis presented at Massey University, Palmerston North, New Zealand (2013).
Wang, H., and van der Donk, W.A., Substrate Selectivity of the Sublancin S-Glycosyltransferase, Journal of the American Chemical Society 133, pp. 16394-16397 (2011).
Garcia De Gonzalo, et al., NMR Structure of the S-Linked Glycopeptide Sublancin 168, ACS Chem. Biol. 9, pp. 796-801 (2014).
Oman, et al., "Sublancin is not a lantibiotic but an S-linked glycopeptide, Nature Chmical Biology," vol. 7, pp. 78-80, Feb. 2011.
Hsieh, Y.S., et al., Synthesis of the Bacteriocin Glycopeptide Sublancin 168 and S-Glycosylated Variants, Organic letters vol. 14, No. 7, pp. 1910-1913, (2012).
Wang, et al., "The Glycosyltransferase Involved in Thurandacin Biosynthesis Catalyzes Both O- and S-Glycosylation", Journal of the American Chemical Society 136, pp. 84-87, Jan. 8, 2014.
Mullegger, et al., "Glycosylation of a Neoglycoprotein by Using Glycosynthase and Thioglycoligase Approaches: The Generation of a Thioglycopratein," Angew. Chem. Int. Ed. 45, pp. 2585-2588 (2006).
Laure Guillotin, et al., Enzymatic Thioglycosylation: Current Knowledge and Challenges, The Royal Society of Chemistry, vol. 40, pp. 178-194, (2014).
Laure Guillotin, et al., "Thioglycoligases: innovative biocatalytic tools for S-glycosylated proteins synthesis," In 11th Carbohydrate Bioengineering Meeting (Espoo, Finland) (2015).
M. Hassan, et al., "Natural antimicrobial peptides from bacteria: characteristics and potential applications to fight against antibiotic resistance," Journal of Applied Microbiology 113, pp. 723-736, (2012).
Cotter, et al., "Bacteriocins—a viable alternative to antibiotics?" Nature reviews Microbiology vol. 11, pp. 95-105 (Feb. 2013).
Izquierdo, et al., "Enterocin 96, a Novel Class II Bacteriocin Produced by Enterococcus Faecalis WHE 96, Isolated from Munster Cheese," Applied and Environmental Microbiology, vol. 75, pp. 4273-4276, (Jul. 2009).
Maky, et al., "Enterocin F4-9, a Novel O-Linked Glycosylated Bacteriocin," Applied and Environmental Microbiology, vol. 81, pp. 4819-4826, (Jul. 2015).
Gantt, et al., "Enzymatic Methods For Glyco (Diversification/Randomization) of Drugs and Small Molecules," Natural Product Reports, Vo. 28, pp. 1811-1853, (2011).
Iwao, et al., "Altered chain-length and glycosylation modify the pharmacokinetics of human serum albumin," ScienceDirect Biochimica et Biophysica Acta, vol. 1794, pp. 634-641, (2008).
Main, P.J., "Investigating the Bacteriocin Library Lactobacillus Plantarum A-1," A thesis presented Massey University, Manuwatu Campus, Palmerston North, New Zealand (2014).
Nant, et al., "Production of an antibacterial substance by bacillus mojavensis strain F412 isolated from a Myanmar shrimp product fermented with boiled rice," Fisheries Science, vol. 81, pp. 795-802, (2015).
Tiwari, et al., "Improved Antimicrobial Activities of Synthetic-Hybrid Bacteriocins Designed From Enterocin E50-52 and Pediocin PA-1," Applied and Environmental Microbiology, vol. 81, pp. 1661-1667, (Mar. 2015).
Wang, et al., "The Bacteriocin Sublancin Attenuates Intestinal Injury in Young Mice Infected With *Staphylococcus aureus*," The Anatomical Record, vol. 297, pp. 1454-1461 (2014).
Venugopal, et al., "Structural, Dynamic, and Chemical Characterization of a Novel S-Glycosylated Bacteriocin," Biochemistry, American Chemical Society, vol. 50, pp. 2748-2755, (2011).
Masias, et al., "28-mer Fragment Derived from Enterocin CRL35 Displays an Unexpected Bactericidal Effect on Listeria Cells," Protein and Peptide Letters 22, pp. 482-488, (2015).
Glycosylatransferase , Group 2 Family Protein, "UniProtKB-C0X1N2 (C0X1N2 ENTFL)," May 26, 2009 (May 26, 2009), XP055400908.
"Enterococcus faecalis V583 plasmid pTEF2, complete sequence.", EMBL29 Mar. 2003 (Mar. 29, 2003), retrieved from EBI accession No. EM_STD:AE016831 Database accession No. AE01683; XP002773411.
"Enterococcus faecalis Enterocin 96 polypeptide, SEQ 92 ", Geneseq09 Apr. 2015 (Apr. 9, 2015), retrieved from EBI accession No. GSP:BBU98419 Database accession No. BBU98419; XP002773162.
Luzhetskyy et al, "Features and applications of bacterial glycosyltransferases: current state and prospects", Applied Microbiology and Biotechnology, Springer, Berlin, DE, vol. 80, No. 6, Sep. 6, 2008 (Sep. 6, 2008), pp. 945-952, XP019654159.

SEQUENCE LISTING

```
<160> NUMBER OF SEQ ID NOS: 20

<210> SEQ ID NO 1
<211> LENGTH: 455
<212> TYPE: PRT
<213> ORGANISM: Artificial Sequence
<220> FEATURE:
<223> OTHER INFORMATION: C-term 6X His tagged recombinant
      Glycosyltransferase protein

<400> SEQUENCE: 1

Met Gly Tyr Ser Glu Asn Phe Ile Ala Asn Asp Trp Phe Asn Val Glu
1               5                   10                  15

Val Phe Asn Lys Asn Lys Tyr Thr Leu Thr Asn Gln Glu Asn Lys Asp
            20                  25                  30

Val Thr Glu Leu Trp Leu Gln Ile Leu Lys Gly Leu Lys Phe Pro Asn
        35                  40                  45

Glu Leu Lys Glu Thr Val Ser Tyr Ser Lys Asn Leu Lys Glu Leu Ser
    50                  55                  60

Leu Lys Thr His Ala Glu Val Ser Val Cys Ile Ile Ala Lys Asn Glu
65                  70                  75                  80

Gln Asp Ser Ile Arg Lys Cys Ile Asn Ser Ile Tyr Glu Phe Ser Asp
                85                  90                  95

Glu Ile Ile Phe Ile Asp Thr Gly Ser Ile Asp Ser Thr Lys Lys Ile
            100                 105                 110

Val Lys Glu Ile Ala Ser Glu Lys Val Lys Ile Phe Asp Tyr Thr Trp
        115                 120                 125

Gln Asp Asp Phe Ser Asp Ala Arg Asn Tyr Ser Ile Gln Lys Ala Ser
    130                 135                 140

Lys Glu Trp Ile Leu Ile Asp Ala Asp Glu Tyr Val Ser Ser Asp
145                 150                 155                 160
```

```
Glu Leu Ile Lys Leu Arg Leu Leu Ile Asp Met Leu Asp Arg Phe Lys
                165                 170                 175

Phe Lys Asp Ser Leu Arg Val Ser Cys Ala Ile Tyr Gln Leu Asp Asn
            180                 185                 190

Val Ile Thr His Gly Gln Ser Arg Leu Phe Arg Asn Asn Asn Lys Ile
        195                 200                 205

Lys Tyr Tyr Gly Leu Ile His Glu Glu Leu Arg Asn Asn Lys Gly Leu
    210                 215                 220

Asp Pro Ile Phe Asn Val Glu Ser Glu Ile Thr Phe Phe His Asp Gly
225                 230                 235                 240

Tyr Lys Glu Ile Leu Arg Lys Gly Lys Cys Glu Arg Asn Ile Arg Leu
                245                 250                 255

Leu Ala Lys Met Leu Glu Lys Glu Pro Asp Asn Val Arg Trp Ala Tyr
            260                 265                 270

Leu Tyr Cys Arg Asp Ser Phe Ser Ile Asn Ser Asn Ile Asp Phe Glu
        275                 280                 285

Lys Ile Leu Leu Pro Phe Leu Ile Lys Asn Met Asp Glu Ser Ile Ser
    290                 295                 300

Cys Glu Asn Ile Leu Leu Thr Asn Tyr Thr His Leu Ile Leu Phe Leu
305                 310                 315                 320

Ile Thr Lys Lys Tyr Ile Ile Asp Gly Lys Ser Ser Leu Ala Ser Lys
                325                 330                 335

Cys Ile Glu Val Leu Glu Lys Met Leu Pro Asn Ser Ser Asp Val Thr
            340                 345                 350

Phe Tyr Lys Phe Leu Asn Lys Gln His Ser Leu Tyr Glu Gln Gln Phe
        355                 360                 365

Glu Phe Leu Lys Glu Val Ile Gln Phe Arg Lys Asn Asn Glu Tyr Asp
    370                 375                 380

Gln Tyr Ser Gln Ile Gly Cys Asn Leu Leu His Tyr Asp Leu Leu Ile
385                 390                 395                 400

Ser Gly Leu Leu Phe Asp Val Lys Ser Tyr Asp Tyr Ser Tyr Gln Tyr
                405                 410                 415

Phe Leu Lys Leu Asp Leu Ala Asn Tyr Phe Ser Glu Leu Glu Ile Pro
            420                 425                 430

Asp Glu Tyr Lys Met Leu Ile Asn Lys Tyr Arg Glu Asn Glu Ser Leu
        435                 440                 445

Glu His His His His His His
    450                 455
```

<210> SEQ ID NO 2
<211> LENGTH: 469
<212> TYPE: PRT
<213> ORGANISM: Artificial Sequence
<220> FEATURE:
<223> OTHER INFORMATION: N-term 6X His tagged recombinant
    Glycosyltransferase protein

<400> SEQUENCE: 2

```
Met His His His His His Ser Ser Gly Val Asp Leu Gly Thr Glu
1               5                   10                  15

Asn Leu Tyr Phe Gln Ser Met Gly Tyr Ser Gly Asn Phe Ile Ala Asn
            20                  25                  30

Asp Trp Phe Asn Val Glu Val Phe Asn Lys Asn Lys Tyr Thr Leu Thr
        35                  40                  45

Asn Gln Glu Asn Lys Asp Val Thr Glu Leu Trp Leu Gln Ile Leu Lys
    50                  55                  60
```

```
Gly Leu Lys Phe Pro Asn Glu Leu Lys Glu Thr Val Ser Tyr Ser Lys
 65                  70                  75                  80

Asn Leu Lys Glu Leu Ser Leu Lys Thr His Ala Glu Val Ser Val Cys
                     85                  90                  95

Ile Ile Ala Lys Asn Glu Gln Asp Ser Ile Arg Lys Cys Ile Asn Ser
                100                 105                 110

Ile Tyr Glu Phe Ser Asp Glu Ile Phe Ile Asp Thr Gly Ser Ile
                115                 120                 125

Asp Ser Thr Lys Lys Ile Val Lys Glu Ile Ala Ser Glu Lys Val Lys
            130                 135                 140

Ile Phe Asp Tyr Thr Trp Gln Asp Asp Phe Ser Asp Ala Arg Asn Tyr
145                 150                 155                 160

Ser Ile Gln Lys Ala Ser Lys Glu Trp Ile Leu Ile Asp Ala Asp
                165                 170                 175

Glu Tyr Val Ser Ser Asp Glu Leu Ile Lys Leu Arg Leu Leu Ile Asp
                180                 185                 190

Met Leu Asp Arg Phe Lys Phe Lys Asp Ser Leu Arg Val Ser Cys Ala
            195                 200                 205

Ile Tyr Gln Leu Asp Asn Val Ile Thr His Gly Gln Ser Arg Leu Phe
            210                 215                 220

Arg Asn Asn Asn Lys Ile Lys Tyr Tyr Gly Leu Ile His Glu Glu Leu
225                 230                 235                 240

Arg Asn Asn Lys Gly Leu Asp Pro Ile Phe Asn Val Glu Ser Glu Ile
                245                 250                 255

Thr Phe Phe His Asp Gly Tyr Lys Glu Ile Leu Arg Lys Glu Lys Cys
                260                 265                 270

Glu Arg Asn Ile Arg Leu Leu Ala Lys Met Leu Glu Lys Glu Pro Asp
            275                 280                 285

Asn Val Arg Trp Ala Tyr Leu Tyr Cys Arg Asp Ser Phe Ser Ile Asn
            290                 295                 300

Ser Asn Ile Asp Phe Glu Lys Ile Leu Leu Pro Phe Leu Ile Lys Asn
305                 310                 315                 320

Met Asp Glu Ser Ile Ser Cys Glu Asn Ile Leu Leu Thr Asn Tyr Thr
                325                 330                 335

His Leu Ile Leu Phe Leu Ile Thr Lys Lys Tyr Ile Ile Asp Gly Lys
            340                 345                 350

Ser Ser Leu Ala Ser Lys Cys Ile Glu Val Leu Glu Lys Met Leu Pro
            355                 360                 365

Asn Ser Ser Asp Val Thr Phe Tyr Lys Phe Leu Asn Lys Gln His Ser
            370                 375                 380

Leu Tyr Glu Gln Gln Phe Glu Phe Leu Lys Glu Val Ile Gln Phe Arg
385                 390                 395                 400

Lys Asn Asn Glu Tyr Asp Gln Tyr Ser Gln Ile Gly Cys Asn Leu Leu
                405                 410                 415

His Tyr Asp Leu Leu Ile Ser Gly Leu Leu Phe Asp Val Lys Ser Tyr
            420                 425                 430

Asp Tyr Ser Tyr Gln Tyr Phe Leu Lys Leu Asp Leu Ala Asn Tyr Phe
            435                 440                 445

Ser Glu Leu Glu Ile Pro Asp Glu Tyr Lys Met Leu Ile Asn Lys Tyr
            450                 455                 460

Arg Glu Asn Glu Ser
465
```

<210> SEQ ID NO 3
<211> LENGTH: 819
<212> TYPE: PRT
<213> ORGANISM: Artificial Sequence
<220> FEATURE:
<223> OTHER INFORMATION: N-term MBP-Glycosyltransferase fusion protein

<400> SEQUENCE: 3

```
Met Lys Ile Glu Glu Gly Lys Leu Val Ile Trp Ile Asn Gly Asp Lys
1               5                   10                  15

Gly Tyr Asn Gly Leu Ala Glu Val Gly Lys Lys Phe Glu Lys Asp Thr
                20                  25                  30

Gly Ile Lys Val Thr Val Glu His Pro Asp Lys Leu Glu Glu Lys Phe
            35                  40                  45

Pro Gln Val Ala Ala Thr Gly Asp Gly Pro Asp Ile Ile Phe Trp Ala
    50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
                100                 105                 110

Ala Leu Ser Leu Ile Tyr Asn Lys Asp Leu Leu Pro Asn Pro Pro Lys
            115                 120                 125

Thr Trp Glu Glu Ile Pro Ala Leu Asp Lys Glu Leu Lys Ala Lys Gly
    130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
                180                 185                 190

Leu Thr Phe Leu Val Asp Leu Ile Lys Asn Lys His Met Asn Ala Asp
            195                 200                 205

Thr Asp Tyr Ser Ile Ala Glu Ala Ala Phe Asn Lys Gly Glu Thr Ala
    210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
                260                 265                 270

Asn Lys Glu Leu Ala Lys Glu Phe Leu Glu Asn Tyr Leu Leu Thr Asp
            275                 280                 285

Glu Gly Leu Glu Ala Val Asn Lys Asp Lys Pro Leu Gly Ala Val Ala
    290                 295                 300

Leu Lys Ser Tyr Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
            340                 345                 350

Ser Gly Arg Gln Thr Val Asp Glu Ala Leu Ala Ala Ala Gln Thr Asn
    355                 360                 365
```

-continued

Ala Ala His Met Tyr Ser Glu Asn Phe Ile Ala Asn Asp Trp Phe Asn
    370                 375                 380

Val Glu Val Phe Asn Lys Asn Lys Tyr Thr Leu Thr Asn Gln Glu Asn
385                 390                 395                 400

Lys Asp Val Thr Glu Leu Trp Leu Gln Ile Leu Lys Gly Leu Lys Phe
                405                 410                 415

Pro Asn Glu Leu Lys Glu Thr Val Ser Tyr Ser Lys Asn Leu Lys Glu
                420                 425                 430

Leu Ser Leu Lys Thr His Ala Glu Val Ser Val Cys Ile Ile Ala Lys
        435                 440                 445

Asn Glu Gln Asp Ser Ile Arg Lys Cys Ile Asn Ser Ile Tyr Glu Phe
450                 455                 460

Ser Asp Glu Ile Ile Phe Ile Asp Thr Gly Ser Ile Asp Ser Thr Lys
465                 470                 475                 480

Lys Ile Val Lys Glu Ile Ala Ser Glu Lys Val Lys Ile Phe Asp Tyr
                485                 490                 495

Thr Trp Gln Asp Asp Phe Ser Asp Ala Arg Asn Tyr Ser Ile Gln Lys
                500                 505                 510

Ala Ser Lys Glu Trp Ile Leu Ile Ile Asp Ala Asp Glu Tyr Val Ser
        515                 520                 525

Ser Asp Glu Leu Ile Lys Leu Arg Leu Leu Ile Asp Met Leu Asp Arg
530                 535                 540

Phe Lys Phe Lys Asp Ser Leu Arg Val Ser Cys Ala Ile Tyr Gln Leu
545                 550                 555                 560

Asp Asn Val Ile Thr His Gly Gln Ser Arg Leu Phe Arg Asn Asn Asn
                565                 570                 575

Lys Ile Lys Tyr Tyr Gly Leu Ile His Glu Leu Arg Asn Asn Lys
                580                 585                 590

Gly Leu Asp Pro Ile Phe Asn Val Glu Ser Glu Ile Thr Phe Phe His
        595                 600                 605

Asp Gly Tyr Lys Glu Ile Leu Arg Lys Glu Lys Cys Glu Arg Asn Ile
610                 615                 620

Arg Leu Leu Ala Lys Met Leu Glu Lys Glu Pro Asp Asn Val Arg Trp
625                 630                 635                 640

Ala Tyr Leu Tyr Cys Arg Asp Ser Phe Ser Ile Asn Ser Asn Ile Asp
                645                 650                 655

Phe Glu Lys Ile Leu Leu Pro Phe Leu Ile Lys Asn Met Asp Glu Ser
                660                 665                 670

Ile Ser Cys Glu Asn Ile Leu Leu Thr Asn Tyr Thr His Leu Ile Leu
        675                 680                 685

Phe Leu Ile Thr Lys Lys Tyr Ile Ile Asp Gly Lys Ser Ser Leu Ala
        690                 695                 700

Ser Lys Cys Ile Glu Val Leu Glu Lys Met Leu Pro Asn Ser Ser Asp
705                 710                 715                 720

Val Thr Phe Tyr Lys Phe Leu Asn Lys Gln His Ser Leu Tyr Glu Gln
                725                 730                 735

Gln Phe Glu Phe Leu Lys Glu Val Ile Gln Phe Arg Lys Asn Asn Glu
                740                 745                 750

Tyr Asp Gln Tyr Ser Gln Ile Gly Cys Asn Leu Leu His Tyr Asp Leu
        755                 760                 765

Leu Ile Ser Gly Leu Leu Phe Asp Val Lys Ser Tyr Asp Tyr Ser Tyr
770                 775                 780

Gln Tyr Phe Leu Lys Leu Asp Leu Ala Asn Tyr Phe Ser Glu Leu Glu

```
            785                 790                 795                 800
Ile Pro Asp Glu Tyr Lys Met Leu Ile Asn Lys Tyr Arg Glu Asn Glu
                805                 810                 815

Ser Leu Glu

<210> SEQ ID NO 4
<211> LENGTH: 48
<212> TYPE: PRT
<213> ORGANISM: Artificial Sequence
<220> FEATURE:
<223> OTHER INFORMATION: Acceptor Substrate 1

<400> SEQUENCE: 4

Met Ser Lys Arg Asp Cys Asn Leu Met Lys Ala Cys Cys Ala Gly Gln
1               5                   10                  15

Ala Val Thr Tyr Ala Ile His Ser Leu Leu Asn Arg Leu Gly Gly Asp
                20                  25                  30

Ser Ser Asp Pro Ala Gly Cys Asn Asp Ile Val Arg Lys Tyr Cys Lys
            35                  40                  45

<210> SEQ ID NO 5
<211> LENGTH: 48
<212> TYPE: PRT
<213> ORGANISM: Artificial Sequence
<220> FEATURE:
<223> OTHER INFORMATION: Acceptor Substrate 2

<400> SEQUENCE: 5

Met Ser Lys Arg Asp Cys Asn Leu Met Lys Ala Cys Cys Ala Gly Gln
1               5                   10                  15

Ala Val Thr Tyr Ala Ile His Ser Leu Leu Asn Arg Leu Gly Gly Asp
                20                  25                  30

Cys Ser Asp Pro Ala Gly Cys Asn Asp Ile Val Arg Lys Tyr Cys Lys
            35                  40                  45

<210> SEQ ID NO 6
<211> LENGTH: 36
<212> TYPE: PRT
<213> ORGANISM: Artificial Sequence
<220> FEATURE:
<223> OTHER INFORMATION: Acceptor Substrate 3

<400> SEQUENCE: 6

Met Ser Lys Arg Asp Cys Asn Leu Met Lys Ala Cys Cys Ala Gly Gln
1               5                   10                  15

Ala Val Thr Tyr Ala Ile His Ser Leu Leu Asn Arg Leu Gly Gly Asp
                20                  25                  30

Ser Ser Asp Pro
            35

<210> SEQ ID NO 7
<211> LENGTH: 32
<212> TYPE: PRT
<213> ORGANISM: Artificial Sequence
<220> FEATURE:
<223> OTHER INFORMATION: Acceptor Substrate 4

<400> SEQUENCE: 7

Ala Val Thr Tyr Ala Ile His Ser Leu Leu Asn Arg Leu Gly Gly Asp
1               5                   10                  15

Ser Ser Asp Pro Ala Gly Cys Asn Asp Ile Val Arg Lys Tyr Cys Lys
                20                  25                  30
```

<210> SEQ ID NO 8
<211> LENGTH: 20
<212> TYPE: PRT
<213> ORGANISM: Artificial Sequence
<220> FEATURE:
<223> OTHER INFORMATION: Acceptor Substrate 5

<400> SEQUENCE: 8

Ala Val Thr Tyr Ala Ile His Ser Leu Leu Asn Arg Leu Gly Gly Asp
1               5                   10                  15

Ser Ser Asp Pro
            20

<210> SEQ ID NO 9
<211> LENGTH: 20
<212> TYPE: PRT
<213> ORGANISM: Artificial Sequence
<220> FEATURE:
<223> OTHER INFORMATION: Acceptor Substrate 6

<400> SEQUENCE: 9

Ala Val Thr Tyr Ala Ile His Ser Leu Leu Asn Arg Leu Gly Gly Asp
1               5                   10                  15

Thr Ser Asp Pro
            20

<210> SEQ ID NO 10
<211> LENGTH: 20
<212> TYPE: PRT
<213> ORGANISM: Artificial Sequence
<220> FEATURE:
<223> OTHER INFORMATION: Acceptor Substrate 7

<400> SEQUENCE: 10

Ala Val Thr Tyr Ala Ile His Ser Leu Leu Asn Arg Leu Gly Gly Glu
1               5                   10                  15

Ser Ser Asp Pro
            20

<210> SEQ ID NO 11
<211> LENGTH: 19
<212> TYPE: PRT
<213> ORGANISM: Artificial Sequence
<220> FEATURE:
<223> OTHER INFORMATION: Acceptor Substrate 8

<400> SEQUENCE: 11

Ala Val Thr Tyr Ala Ile His Ser Leu Leu Asn Arg Leu Gly Gly Asp
1               5                   10                  15

Ser Ala Pro

<210> SEQ ID NO 12
<211> LENGTH: 19
<212> TYPE: PRT
<213> ORGANISM: Artificial Sequence
<220> FEATURE:
<223> OTHER INFORMATION: Acceptor Substrate 9

<400> SEQUENCE: 12

Ala Val Thr Tyr Ala Ile His Ser Leu Leu Asn Arg Leu Gly Gly Asp
1               5                   10                  15

Ser Ser Pro

```
<210> SEQ ID NO 13
<211> LENGTH: 19
<212> TYPE: PRT
<213> ORGANISM: Artificial Sequence
<220> FEATURE:
<223> OTHER INFORMATION: Acceptor Substrate 10

<400> SEQUENCE: 13

Ala Val Thr Tyr Ala Ile His Ser Leu Leu Asn Arg Leu Gly Gly Asp
1               5                   10                  15

Ser Arg Pro

<210> SEQ ID NO 14
<211> LENGTH: 19
<212> TYPE: PRT
<213> ORGANISM: Artificial Sequence
<220> FEATURE:
<223> OTHER INFORMATION: Acceptor Substrate 11

<400> SEQUENCE: 14

Ala Val Thr Tyr Ala Ile His Ser Leu Leu Asn Arg Leu Gly Gly Asp
1               5                   10                  15

Ser Thr Pro

<210> SEQ ID NO 15
<211> LENGTH: 18
<212> TYPE: PRT
<213> ORGANISM: Artificial Sequence
<220> FEATURE:
<223> OTHER INFORMATION: Acceptor Substrate 12

<400> SEQUENCE: 15

Ala Val Thr Tyr Ala Ile His Ser Leu Leu Asn Arg Leu Gly Gly Asp
1               5                   10                  15

Ser Ser

<210> SEQ ID NO 16
<211> LENGTH: 16
<212> TYPE: PRT
<213> ORGANISM: Artificial Sequence
<220> FEATURE:
<223> OTHER INFORMATION: Acceptor Substrate 13

<400> SEQUENCE: 16

Ala Ile His Ser Leu Leu Asn Arg Leu Gly Gly Asp Ser Ser Asp Pro
1               5                   10                  15

<210> SEQ ID NO 17
<211> LENGTH: 15
<212> TYPE: PRT
<213> ORGANISM: Artificial Sequence
<220> FEATURE:
<223> OTHER INFORMATION: Acceptor Substrate 14

<400> SEQUENCE: 17

Ile His Ser Leu Leu Asn Arg Leu Gly Gly Asp Ser Ser Asp Pro
1               5                   10                  15

<210> SEQ ID NO 18
<211> LENGTH: 1343
<212> TYPE: DNA
<213> ORGANISM: Artificial Sequence
<220> FEATURE:
<223> OTHER INFORMATION: Expression cassette encoding  GT-CTH
```

<400> SEQUENCE: 18

```
catgggctat tctgaaaatt ttattgctaa tgactggttt aatgtagagg tatttaataa      60
aaataagtat actttaacga accaagagaa taaagatgta acagaattat ggttacaaat     120
tttaaagggg ctaaagttcc ccaacgaatt aaaggaaact gtcagttact ctaaaaattt     180
aaaagaatta tctttaaaaa ctcacgcaga agtatctgta tgtattattg ctaagaatga     240
acaggattca ataagaaaat gtattaatag tatctatgaa ttttcagatg aaattatatt     300
tattgataca ggatcaattg attcgacaaa aaaaatagta aaagaaatag caagcgaaaa     360
agtaaaaata tttgattata cttggcaaga tgattttttca gatgcgagaa attattcaat     420
acaaaaagca agtaaagaat ggatattaat tattgatgca gatgaaatg tatcttcaga      480
tgagcttatc aaattaaggc tcttaataga tatgttagac aggtttaaat ttaaagattc     540
attaagagtt agttgtgcaa tatatcaatt agataatgtt atcacacatg gccaaagtcg     600
attatttaga aacaataata aaattaagta ttatggtcta atacatgaag agttgaggaa     660
caacaaagga ttagatccaa tttttaacgt tgaaagtgag attactttttt tccatgacgg     720
ttacaaagaa atacttagga aagagaagtg tgaaagaaac ataaggctac tagctaagat     780
gttagaaaaa gagccagaca atgttagatg ggcatacttg tattgtagag attcattttc     840
tataaattcc aacattgatt ttgaaaaaat tctacttcca ttttttaataa agaatatgga     900
tgaaagtata tcatgtgaga atatcctact tacaaactat actcatttaa tcctatttct     960
tattactaag aaatatataa ttgatgggaa aagctcactt gcaagtaaat gtatagaggt    1020
gttagaaaaa atgctaccta actcttctga tgttactttt tacaaatttt taaataaaca    1080
gcatagtttg tatgaacaac aatttgaatt tttaaaagaa gtaattcaat ttagaaaaaa    1140
taatgaatat gatcaatata gccaaatagg gtgtaattta ttcactatg atttattaat     1200
ttcaggatta cttttttgatg ttaagtctta tgattattca tatcaatact ttttaaaatt    1260
agatttagct aactatttt ctgaattaga gattcctgat gaatacaaaa tgttaataaa     1320
taagtatcgg gagaatgaat cac                                            1343
```

<210> SEQ ID NO 19
<211> LENGTH: 1346
<212> TYPE: DNA
<213> ORGANISM: Artificial Sequence
<220> FEATURE:
<223> OTHER INFORMATION: Expression cassette encoding MBP-NTH

<400> SEQUENCE: 19

```
catgggctat tctgaaaatt ttattgctaa tgactggttt aatgtagagg tatttaataa      60
aaataagtat actttaacga accaagagaa taaagatgta acagaattat ggttacaaat     120
tttaaagggg ctaaagttcc ccaacgaatt aaaggaaact gtcagttact ctaaaaattt     180
aaaagaatta tctttaaaaa ctcacgcaga agtatctgta tgtattattg ctaagaatga     240
acaggattca ataagaaaat gtattaatag tatctatgaa ttttcagatg aaattatatt     300
tattgataca ggatcaattg attcgacaaa aaaaatagta aaagaaatag caagcgaaaa     360
agtaaaaata tttgattata cttggcaaga tgattttttca gatgcgagaa attattcaat     420
acaaaaagca agtaaagaat ggatattaat tattgatgca gatgaaatg tatcttcaga      480
tgagcttatc aaattaaggc tcttaataga tatgttagac aggtttaaat ttaaagattc     540
attaagagtt agttgtgcaa tatatcaatt agataatgtt atcacacatg gccaaagtcg     600
attatttaga aacaataata aaattaagta ttatggtcta atacatgaag agttgaggaa     660
```

```
caacaaagga ttagatccaa tttttaacgt tgaaagtgag attactttt tccatgacgg      720 ttacaaagaa atacttagga aagagaagtg tgaaagaaac ataaggctac tagctaagat      780
gttagaaaaa gagccagaca atgttagatg gcatacttg tattgtagag attcattttc      840
tataaattcc aacattgatt tgaaaaaat tctacttcca tttttaataa agaatatgga      900
tgaaagtata tcatgtgaga atatcctact tacaaactat actcatttaa tcctatttct      960
tattactaag aaatatataa ttgatgggaa aagctcactt gcaagtaaat gtatagaggt     1020
gttagaaaaa atgctaccta actcttctga tgttacttt tacaaatttt taaataaaca     1080
gcatagtttg tatgaacaac aatttgaatt tttaaaagaa gtaattcaat ttagaaaaaa     1140
taatgaatat gatcaatata gccaaatagg gtgtaattta ttacactatg atttattaat     1200
ttcaggatta cttttgatg ttaagtctta tgattattca tatcaatact ttttaaaatt     1260
agatttagct aactattttt ctgaattaga gattcctgat gaatacaaaa tgttaataaa     1320
taagtatcgg gagaatgaat catgac                                          1346

<210> SEQ ID NO 20
<211> LENGTH: 1340
<212> TYPE: DNA
<213> ORGANISM: Artificial Sequence
<220> FEATURE:
<223> OTHER INFORMATION: Expression cassette encoding MBP-GT

<400> SEQUENCE: 20
tatgtattct gaaaatttta ttgctaatga ctggtttaat gtagaggtat ttaataaaaa       60
taagtatact ttaacgaacc aagagaataa agatgtaaca gaattatggt tacaaatttt      120
aaaagggcta aagttcccca acgaattaaa ggaaactgtc agttactcta aaaatttaaa      180
agaattatct ttaaaaactc acgcagaagt atctgtatgt attattgcta agaatgaaca      240
ggatccaata agaaaatgta ttaatagtat ctatgaattt tcagatgaaa ttatatttat      300
tgatacagga tcaattgatt cgacaaaaaa aatagtaaaa gaaatagcaa gcgaaaaagt      360
aaaaatattt gattatactt ggcaagatga ttttcagat gcgagaaatt attcaataca      420 aaagcaagt aaagaatgga tattaattat tgatgcagat gaatatgtat cttcagatga      480
gcttatcaaa ttaaggctct aatagatat gttagacagg tttaaattta agattcatt      540 aagagttagt tgtgcaatat atcaattaga taatgttatc acacatggcc aaagtcgatt      600
atttagaaac aataataaaa ttaagtatta tggtctaata catgaagagt tgaggaacaa      660
caaaggatta gatccaattt ttaacgttga agtgagatt actttttcc atgacggtta      720 caaagaaata cttaggaaag agaagtgtga agaaacata aggctactag ctaagatgtt      780
agaaaaagag ccagacaatg ttagatgggc atacttgtat tgtagagatt cattttctat      840
aaattccaac attgattttg aaaaaattct acttccattt ttaataaga atatggatga      900 aagtatatca tgtgagaata tcctacttac aaactatact catttaatcc tatttcttat      960
tactaagaaa tatataattg atgggaaaag ctcacttgca agtaaatgta tagaggtgtt     1020
agaaaaaatg ctacctaact cttctgatgt tacttttac aaattttaa ataaacagca     1080 tagtttgtat gaacaacaat ttgaattttt aaaagaagta attcaattta gaaaaaataa     1140
tgaatatgat caatatagcc aaatagggtg taatttatta cactatgatt tattaatttc     1200
```

```
aggattactt tttgatgtta agtcttatga ttattcatat caatactttt taaaattaga    1260
tttagctaac tatttttctg aattagagat tcctgatgaa tacaaaatgt taataaataa    1320
gtatcgggag aatgaatcac                                                1340
```

MULTIFUNCTIONAL RECOMBINANT NUCLEOTIDE DEPENDENT GLYCOSYLTRANSFERASE PROTEIN AND ITS METHOD OF GLYCOSYLATION THEREOF

CROSS-REFERENCE TO RELATED APPLICATIONS

This application is a National Stage Entry under 35 U.S.C. § 371 of International Patent Application No. PCT/IN2007/050116, filed Mar. 3, 2017, the entire contents of which are incorporated herein by reference.

SEQUENCE LISTING

The instant application contains a Sequence Listing which has been submitted in ASCII format via EFS-Web and is hereby incorporated by reference in its entirety. Said ASCII copy, created on Aug. 13, 2020, is named CSIR0045PA_P_FR100282_US.txt and is 26 KB in size.

FIELD OF THE INVENTION

The present invention generally relates to a multifunctional recombinant nucleotide dependent glycosyltransferase protein and its method of glycosylation thereof. In particular, the invention relates to one pot synthesis of disaccharide glycan on to the acceptor substrate and thereby generating O- and/or S-glycosylated product including neo-glycopeptide and glycosylated antimicrobial peptide by using multifunctional recombinant nucleotide dependent glycosyltransferase.

BACKGROUND OF THE INVENTION

Glycosylation is the enzymatic process that attaches glycans to proteins, lipids or other organic molecules. Glycosylation is an important co-translational or post-translational modification. Many industrial and therapeutic proteins are glycoproteins harboring different types of glycans. Hence, glycosylation of these proteins is important for structure, function, host-pathogen interactions, biomimicry etc (Sola, R. J., and Griebenow, K. (2009). Effects of glycosylation on the stability of protein pharmaceuticals. J Pharm Sci 98, 1223-1245, Sola, R. J., and Griebenow, K. (2010). Glycosylation of therapeutic proteins: an effective strategy to optimize efficacy. BioDrugs 24, 9-21, Shental-Bechor, D., and Levy, Y. (2008). Effect of glycosylation on protein folding: a close look at thermodynamic stabilization. Proc Natl Acad Sci USA 105, 8256-8261, Vasudevan, D., and Haltiwanger, R. S. (2014). Novel roles for O-linked glycans in protein folding. Glycoconjugate journal 31, 417-426).

In eukaryotes, typically, majority of proteins are synthesized in the rough endoplasmic reticulum, which undergo glycosylation wherein glycosylation is an enzyme directed site-specific process. Glycosylation also happens in the cytoplasm and nucleus as the O-GlcNAc modification. Therefore, the proteins or peptides that are not glycosylated naturally but in vitro are termed neo-glycoproteins or neo-glycopeptides and usually possess better bio-activity and stability.

Hence, protein or peptide glycosylation can be achieved in vitro, either by enzymatic means or by chemical means. Enzymatic glycosylation is a preferred route for its specificity, affordability and process simplicity provided suitable and applicable glycosyltransferases are available. The advantage of using glycosyltransferases for generation of glyco-conjugate is that the glycosidic linkages formed by these enzymes are highly stereo and regio-specific (Hanson, S., Best, M., Bryan, M. C., and Wong, C. H. (2004). Chemoenzymatic synthesis of oligosaccharides and glyco-proteins. Trends in biochemical sciences 29, 656-663, Katayama, H., Asahina, Y., and Hojo, H. (2011). Chemical synthesis of the S-linked glycopeptide, sublancin. Journal of peptide science: an official publication of the European Peptide Society 17, 818-821, Zhang, Y., Muthana, S. M., Farnsworth, D., Ludek, O., Adams, K., Barchi, J. J., Jr., and Gildersleeve, J. C. (2012). Enhanced epimerization of glycosylated amino acids during solid-phase peptide synthesis. Journal of the American Chemical Society 134, 6316-6325).

Generally, glycosyltransferase catalyzes a specific linkage of specific sugar donor residues to other specific acceptor molecules, which include a peptide, protein, an oligosaccharide or lipid. Therefore, synthesis of a glyco-conjugate harboring a glycan that is composed of more than one sugar necessitates the use of more than one glycosyltransferases for each independent saccharide unit being transferred. Traditionally known glycosyltransferases are eukaryotic proteins of which most are membrane bound and difficult for expression and purification. Accordingly, these eukaryotic proteins are less amenable for in vitro applications.

Last decade of $20^{th}$ century saw discovery of bacterial glycosyltransferases that are capable of N-, O- and recently characterized S-glycosylation. Most of these proteins are smaller, cytoplasmic and unique in specificities. Thus, providing an opportunity to identify and create novel tools for useful glycosylation in protein or peptides of miscellaneous interest. For example EP Pat. No. 2,049,144B1 (E.P. Patent No. EP2049144 B1 7/2014 Shawn Defrees A61K47/48) discloses method of preparing glycosylated polypeptides using short enzyme recognized O-linked glycosylation sequences (O-linked Sequon).

The U.S. Pat. No. 7,338,933 titled "O-linked glycosylation of peptides" (U.S. Pat. No. 7,338,933 B2 3/2008 Shawn Defrees et al 514/11.4) discloses enzymatic glyco-conjugation reactions specifically targeted to O-linked glycosylation sites and to glycosyl residues (glycan) that are attached to O-linked glycosylation sites. The targeted O-linked glycosylation sites can be sites, native to a wild-type peptide or, alternatively, they can be introduced into a peptide by mutation. The polypeptides of the invention include glyco-conjugates in which, a species, such as a water-soluble polymer, a therapeutic agent of a biomolecule is covalently linked through an intact O-linked glycosyl residue to the polypeptide. Accordingly, the invention provides polypeptides comprising mutated sites suitable for O-linked glycosylation and pharmaceutical compositions thereof. In addition, the invention provides method of making such polypeptides and using such polypeptides and/or pharmaceutical compositions thereof for therapeutic treatments. However, the invention primarily focuses on transfer of monosaccharide and thereby creating O-linked glycosylation.

The U.S. Pat. No. 6,379,933 titled "Method of transferring at least two saccharide units with a polyglycosyltransferase" (U.S. Pat. No. 6,379,933 B1 4/2002 Karl F. Johnson et al 435/97) discloses a method of transferring at least two saccharide units with a polyglycosyltransferase, a polyglycosyltransferase and a gene encoding such a polyglycosyltransferase. In particular, the invention involves method of transferring at least two saccharide units with a polyglycosyltransferase, which transfers both GlcNAc, and GalNAc, from the corresponding sugar nucleotides to a sugar acceptor. However, the invention is specific for and focuses on biosynthesis of oligosaccharides using a polyglycosyltransferase.

The European patent, numbered EP 2,049,144 titled "Glycosylation of peptides via O-linked glycosylation sequences" (E.P. Patent No EP2049144 B8 2/2015 Shawn Defrees C12P21/00) discloses a method of preparing glycosylated polypeptides using short enzyme-recognized O-linked glycosylation sequences. Accordingly, the invention provides targeted glycosylation sequence introduced into a parent polypeptide (e.g., wild-type polypeptide) by mutation creating a mutant polypeptide that includes a glycosylation sequence, wherein this glycosylation sequence is not present, or not present at the same position, in the corresponding parent polypeptide (exogenous glycosylation sequence). Such mutant polypeptides are termed herein "sequon polypeptides". Accordingly, the invention provides sequon polypeptides that include one or more O-linked glycosylation sequence in accordance with the invention. In one embodiment, each glycosylation sequence is a substrate for an enzyme, such as a glycosyltransferase, such as a GalNAc-transferase (e.g., GalNAc-T2). Hence, the invention focuses on O-linked glycosylation and conjugation between a glycosylated or non-glycosylated sequon polypeptide and a polymeric modifying group such as poly (ethylene glycol) and methoxy-poly (ethylene glycol) (m-PEG).

The PCT application, numbered WO/2008/151258 titled "O-linked glycosylation using N-Acetylglycosaminyl transferases" (U.S. Patent No. WO2008151258 A3 2/2009 Shawn Defrees et al C12N9/10) discloses covalent conjugates between a polypeptide and a modifying group, such as a water-soluble polymer (e.g., Poly Ethylene Glycol). The amino acid sequence of the polypeptide includes one or more O-linked glycosylation sequence, each being a substrate for a GlcNAc transferase. The modifying group is covalently linked to the polypeptide via a glycosyl-linking group interposed between and covalently linked to both the polypeptide and the modifying group. In one embodiment, a glucosamine linking group is directly attached to an amino acid residue of the O-linked glycosylation sequence. Accordingly, each glycosylation sequence serves as a substrate for GlcNAc transferase, wherein the method involves transfer of one sugar to given residue at a time creating monosaccharide glycan.

The PCT application numbered WO/2004/009793 titled "Synthesis of glycoproteins using bacterial glycosyltransferases" (U.S. Patent No. WO2004009793 A2 1/2004 Daniel James Bezila et al C12P21/02) discloses methods to use the fucosyltransferases from *Helicobacter pylori* to synthesize oligosaccharides, glycoproteins, and glycolipids. The method involves transfer of a fucose residue from a donor substrate to an acceptor substrate in the presence of α-1, 3/4-fucosyltranferase proteins. Hence, the invention primarily focuses on efficient production of fucosylated oligosaccharides.

The European patent numbered EP 1,981,977 titled "Production of polysialic acid containing glycoconjugates using a self-priming polysialyltransferase" (E.P. Patent No. EP1981977A4 4/2010 Warren-wakarchuk et al C12N15/63, Lindhout, T., Iqbal, U., Willis, L. M., Reid, A. N., Li, J., Liu, X., Moreno, M., and Wakarchuk, W. W. (2011). Site-specific enzymatic polysialylation of therapeutic proteins using bacterial enzymes. Proc Natl Acad Sci USA 108, 7397-7402) discloses site specific enzymatic polysialylation of therapeutic proteins using bacterial enzymes. The patent describes an enzyme which can transfer at least three sialic acid residues on to a glycoprotein having a terminal galactose residue pre attached to it. In fact, product(s) derived using our method can be useful input(s) for such enzyme.

The NCBI article, numbered 1002/chem.201405692 titled "Synthesis of the antimicrobial S-linked glycopeptide, glycocin F (Brimble, M. A., Edwards, P. J., Harris, P. W., Norris, G. E., Patchett, M. L., Wright, T. H., Yang, S. H., and Carley, S. E. (2015). Synthesis of the antimicrobial S-linked glycopeptide, glycocin F. Chemistry 21, 3556-3561, Stepper, J., Shastri, S., Loo, T. S., Preston, J. C., Novak, P., Man, P., Moore, C. H., Havlicek, V., Patchett, M. L., and Norris, G. E. (2011). Cysteine S-glycosylation, a new post-translational modification found in glycopeptide bacteriocins. FEBS Lett 585, 645-650, Kerr, A. P. (2013). The bacteriostatic spectrum and inhibitory mechanism of glycocin F, a bacteriocin from *Lactobacillus plantarum* KW30. In Microbiology (Palmerston North, New Zealand, Massey University) discloses the first total synthesis of glycocin F, a uniquely di-glycosylated antimicrobial peptide bearing a rare S-linked N-acetylglucosamine (GlcNAc) moiety in addition to an O-linked GlcNAc, has been accomplished using a native chemical ligation strategy. The synthetic and naturally occurring peptides were compared by RP-HPLC, mass spectrometry, NMR and CD spectroscopy, and their stability towards chymotrypsin digestion and antimicrobial activity were measured. This is the first comprehensive structural and functional comparison of a naturally occurring glycocin with an active synthetic analogue.

The NCBI article, numbered 1021/ja2075168 and 1038/nchembio.509 titled "Substrate selectivity of the sublancin S-glycosyltransferase (Wang, H., and van der Donk, W. A. (2011). Substrate selectivity of the sublancin S-glycosyltransferase. Journal of the American Chemical Society 133, 16394-16397) and Sublancin is not a lantibiotic but an S-linked glycopeptide (Oman, T. J., Boettcher, J. M., Wang, H., Okalibe, X. N., and van der Donk, W. A. (2011). Sublancin is not a lantibiotic but an S-linked glycopeptide. Nat Chem Biol 7, 78-80), respectively, disclose SunS a novel S-glycosyltransferase involved in the biosynthesis of the antimicrobial peptide sublancin. SunS selectively modifies cysteine22 in a 37 amino acid peptide substrate SunA and can accept a variety of NDP sugars. Hence the study reports the substrate selectivity with regard to the peptide substrate and the antimicrobial activity of the resulting sublancin analogues (Garcia De Gonzalo, C. V., Zhu, L., Oman, T. J., and van der Donk, W. A. (2014). NMR structure of the S-linked glycopeptide sublancin 168. ACS chemical biology 9, 796-801, Hsieh, Y. S., Wilkinson, B. L., O'Connell, M. R., Mackay, J. P., Matthews, J. M., and Payne, R. J. (2012). Synthesis of the bacteriocin glycopeptide sublancin 168 and S-glycosylated variants. Organic letters 14, 1910-1913,). The results suggest that SunS recognizes an α-helix N-terminal of the cysteine to be glycosylated, which is present in a flexible linker. Interestingly, when cysteine22 is mutated, sugar attachment is not required for sublancin antimicrobial activity. Furthermore, the sublancin-producing strain *Bacillus subtilis* 168 also becomes susceptible to such mutants. Therefore, the data suggest that S-glycosylation may be important for self-resistance/immunity in host to its self-produced bacteriocin.

The NCBI article, numbered 1021/ja411159k titled "The glycosyltransferase involved in thurandacin biosynthesis catalyzes both O- and S-glycosylation" (Wang, H., Oman, T. J., Zhang, R., Garcia De Gonzalo, C. V., Zhang, Q., and van der Donk, W. A. (2014). The glycosyltransferase involved in thurandacin biosynthesis catalyzes both O- and S-glycosylation. Journal of the American Chemical Society 136, 84-87) discloses discovery of a second S-glycosyltransferase, ThuS, and shows that ThuS catalyzes both S-glycosylation of the thiol of cysteine and O-glycosylation of the hydroxyl group of serine in peptide substrates. ThuS-catalyzed S-glycosylation is more efficient than O-glycosylation and the enzyme demonstrates high tolerance with respect to both nucleotide sugars and peptide substrates. The biosynthesis of the putative products of the thuS gene cluster are reconstituted in vitro and the resulting S-glycosylated peptides thurandacin A and thurandacin B exhibit highly selective antimicrobial activity towards *Bacillus thuringiensis*.

The Wiley online article numbered 1002/anie.200503900 titled "Glycosylation of a Neo glycoprotein by using glycosynthase and thioglycoligase approaches: The generation of a thioglycoprotein" (Mullegger, J., Chen, H. M., Warren, R. A., and Withers, S. G. (2006). Glycosylation of a neoglycoprotein by using glycosynthase and thioglycoligase approaches: the generation of a thioglycoprotein. Angewandte Chemie (International ed in English) 45, 2585-2588) discloses glycosylation of a neo-glycoprotein achieved by quantitative yields by using a glycosynthase or a thioglycoligase. The resulting glycoproteins function as good acceptors for glycosyl transferases, and the thioglycoprotein is proved to be resistant to glycosidase digestion. Hence the established technology will enable the remodeling of natural glycoproteins to make them more stable against degradation in serum. (Laure Guillotin, P. L., Richard Daniellou (2014). Enzymatic thioglycosylation: current knowledge and challenges, Vol 40, Laure Guillotin, P. L., Richard Daniellou (2015). Thioglycoligases: innovative biocatalytic tools for S-glycosylated proteins synthesis. In 11th Carbohydrate Bioengineering Meeting (Espoo, Finland).

In the view of foregoing, there is ongoing need for an improved method that creates novel glycans like a disaccharide and thereby generates O- and/or S-glycosylated neo-glycopeptides including antimicrobial peptides (Hassan, M., Kjos, M., Nes, I. F., Diep, D. B., and Lotfipour, F. (2012). Natural antimicrobial peptides from bacteria: characteristics and potential applications to fight against antibiotic resistance. Journal of applied microbiology 113, 723-736, Cotter, P. D., Ross, R. P., and Hill, C. (2013). Bacteriocins—a viable alternative to antibiotics? Nature reviews Microbiology 11, 95-105, Izquierdo, E., Wagner, C., Marchioni, E., Aoude-Werner, D., and Ennahar, S. (2009). Enterocin 96, a novel class II bacteriocin produced by *Enterococcus faecalis* WHE 96, isolated from Munster cheese. Appl Environ Microbiol 75, 4273-4276, Maky, M. A., Ishibashi, N., Zendo, T., Perez, R. H., Doud, J. R., Karmi, M., and Sonomoto, K. (2015). Enterocin F4-9, a Novel O-Linked Glycosylated Bacteriocin. Appl Environ Microbiol 81, 4819-4826, Masias, E., Sanches, P. R., Dupuy, F. G., Acuna, L., Bellomio, A., Cilli, E., Saavedra, L., and Minahk, C. (2015). 28-mer Fragment Derived from Enterocin CRL35 Displays an Unexpected Bactericidal Effect on *Listeria* Cells. Protein and peptide letters 22, 482-488) by using minimal number of glycosyltransferases necessary to form different glycosidic bonds (Gantt, R. W., Peltier-Pain, P., and Thorson, J. S. (2011). Enzymatic methods for glyco (diversification/randomization) of drugs and small molecules. Natural product reports 28, 1811-1853). Moreover, the resultant disaccharide-conjugates provide for more bioactive species than corresponding monosaccharide linked conjugates (Iwao, Y., Hiraike, M., Kragh-Hansen, U., Kawai, K., Suenaga, A., Maruyama, T., and Otagiri, M. (2009). Altered chain-length and glycosylation modify the pharmacokinetics of human serum albumin. BiochimBiophysActa 1794, 634-641).

SUMMARY OF THE INVENTION

Accordingly, the present invention provides a multifunctional recombinant nucleotide dependent glycosyltransferase protein and its method of glycosylation thereof. It is an object of the present invention to provide O and/or S-linked di-glycosylated product by contacting donor substrate with acceptor substrate in the presence of multifunctional recombinant nucleotide dependent glycosyltransferase enzyme, which catalyzes the reaction. Hence, the present invention provides one pot synthesis of disaccharide glycan on to serine or threonine or cysteine residue in acceptor substrate.

It is yet another object of the present invention to provide glyco-randomization/glyco-diversification and synthesize at least four different disaccharide glycans on to the acceptor. The method of glyco-diversification comprises the generation of a mixture of un-modified, mono-glucosylated or mono-galactosylated and di-glucosylated or di-galactosylated glycoforms as product, followed by separation and purification of these various glycoforms using RP-HPLC and then incubating the purified mono-glucosylated or mono-galactosylated glycoform with recombinant nucleotide dependent glycosyltransferase enzyme and UDP-galactose or UDP-glucose, respectively to obtain glyco-diversified (di-glycosylated) product.

It is yet another object of the present invention to provide a method of generating such glyco-diversified (di-glycosylated) products that exhibit differential bioactivity, wherein bioactivity is modulated by the nature and size of the glycan attached to the products.

Therefore, the present invention provides sugar enriched products by constructing a disaccharide and not just a monosaccharide glycan at a single site using single enzyme reaction. The invention also provides components to carry out glycosylation in vivo in a prokaryotic host and is useful for generating glycosylation in acceptor substrate where acceptor sites are not surface accessible in vitro.

In an embodiment of the present invention it provides a multifunctional recombinant nucleotide dependent glycosyltransferase protein having amino acid sequence selected from the group consisting of SEQ ID NO. 1, SEQ ID NO. 2, SEQ ID NO. 3 and variants thereof.

In an embodiment of the present invention it provides the multifunctional recombinant nucleotide dependent glycosyltransferase protein wherein the protein corresponding to SEQ ID NO: 1 is C-terminal 6x-His tagged recombinant glycosyltransferase protein.

In an embodiment of the present invention it provides the multifunctional recombinant nucleotide dependent glycosyltransferase protein wherein the protein corresponding to SEQ ID NO: 2 is N-terminal 6x-His tagged recombinant glycosyltransferase protein.

In an embodiment of the present invention it provides the multifunctional recombinant nucleotide dependent glycosyltransferase protein wherein the protein corresponding to SEQ ID NO: 3 is N-terminal MBP glycosyltransferase fusion protein.

In an embodiment of the present invention it provides an in vitro one pot method for synthesis of O-linked and/or S-linked di-glycosylated products, wherein the method comprises of:
  a. providing a mixture of a donor substrate and an acceptor substrate in a ratio of 20:1, wherein the donor substrate is an activated nucleotide sugar selected from the group consisting of saccharide-UDP, saccharide-GDP, and related nucleotide sugars thereof and the acceptor substrate comprises a peptide or polypeptide having amino acid sequence selected from the group consisting of SEQ ID NO.: 4, SEQ ID NO.: 5, SEQ ID NO.: 6, SEQ ID NO.: 7, SEQ ID NO.: 8, SEQ ID NO.: 9, SEQ ID NO.: 10, SEQ ID NO.: 11, SEQ ID NO.: 12, SEQ ID NO.: 13, SEQ ID NO.: 14, SEQ ID NO.: 15, SEQ ID NO.: 16 and SEQ ID NO.: 17.
  b. providing a multifunctional recombinant nucleotide dependent glycosyltransferase protein having amino acid sequence selected from the group consisting of SEQ ID NO. 1, SEQ ID NO. 2, and SEQ ID NO. 3;
  c. contacting a multifunctional recombinant nucleotide dependent glycosyltransferase protein obtained in step (b) with the mixture obtained in step (a);
  d. reacting the donor substrate and the acceptor substrate in presence of the multifunctional recombinant nucleotide dependent glycosyltransferase protein, wherein the glycosyltransferase protein catalyzes the transfer of plurality of saccharide moieties from the donor substrate to serine, threonine or cysteine residue in the acceptor substrate to obtain the O-linked and/or S-linked di-glycosylated products.

In yet another embodiment of the present invention it provides the method wherein the donor substrate saccharide-UDP sugar is UDP-glucose or UDP-galactose and the GDP sugar is GDP-glucose or GDP-galactose.

In yet another embodiment of the present invention it provides the method wherein the acceptor substrate comprises peptide or polypeptide having at least one exogenous or endogenous copy of amino acid sequence corresponding to minimal acceptor sequence of SEQ ID NO.: 17 and variants thereof.

In yet another embodiment of the present invention it provides the method wherein the amino acid residue substituted in the variant of minimal acceptor sequence of SEQ ID NO.: 17 is selected from the group consisting of D11E, S12T, S12C, S13T, S14R and S14A.

In yet another embodiment of the present invention it provides an expression cassette consisting of a gene encoding multifunctional recombinant nucleotide dependent glycosyltransferase protein having sequence selected from the group consisting of SEQ ID No.: 18, SEQ ID No.: 19 and SEQ ID No.: 20.

In yet another embodiment of the present invention it provides the method wherein the di-glycosylated product is an antimicrobial peptide.

In yet another embodiment of the present invention it provides the method wherein the antimicrobial peptide is enterocin 96 and glycol-variant thereof.

In yet another embodiment of the present invention it provides a method of producing a mixture of glycosylated products of acceptor substrates comprising peptide or polypeptide having amino acid sequence selected from the group consisting of SEQ ID NO.: 4, SEQ ID NO.: 5, SEQ ID NO.: 6, SEQ ID NO.: 7, SEQ ID NO.: 8, SEQ ID NO.: 9, SEQ ID NO.: 10, SEQ ID NO.: 11, SEQ ID NO.: 12, SEQ ID NO.: 13, SEQ ID NO.: 14, SEQ ID NO.: 15, SEQ ID NO.: 16, SEQ ID NO.: 17 wherein the enzyme: substrate ratio in the method is modulated to produce a mixture of un-modified, mono-glycosylated and di-glycosylated product.

In yet another embodiment of the present invention it provides a method of producing a mixture of glyco-diversified products using the di-glycosylated product to obtain a mixture of glyco-diversified products, wherein the mixture comprises mono-glycosylated and di-glycosylated products.

In yet another embodiment of the present invention it provides the method wherein the di-glycosylated product is incubated with an exoglycosidase that catalyzes removal of terminal saccharide moieties from the di-glycosylated products to obtain mono-glycosylated products;

In yet another embodiment of the present invention it provides the method wherein the exoglycosidase is selected from β-glucosidase and β-galactosidase.

In yet another embodiment of the present invention it provides the method wherein the method additionally comprises separating and purifying the un-modified, mono-glycosylated and di-glycosylated product using RP-HPLC.

BRIEF DESCRIPTION OF TABLES AND DRAWINGS

Table 1 illustrates the table comprising details on cloning and expression of multifunctional recombinant nucleotide dependent glycosyltransferase in different bacterial expression vectors in accordance with the present invention.

Table 2 illustrates the table comprising information on various amino acid sequences and nucleotide sequences in accordance with the present invention.

Table 3 comprising information on In vitro glycosyltransferase activity status of the mutants.

FIG. 1 illustrates the vector maps of protein expression vectors encoding multifunctional recombinant nucleotide dependent glycosyltransferase enzyme, described in Table 1, which include FIG. 1a: GTpET28a encoding multifunctional recombinant nucleotide dependent glycosyltransferase enzyme in fusion with C-term His tag (GT-CTH), FIG. 1b: GTpNIC28-Bsa4 encoding multifunctional recombinant nucleotide dependent glycosyltransferase enzyme in fusion with N-term His tag (GT-NTH), FIG. 1c: GTpMAL-c2X encoding multifunctional recombinant nucleotide dependent glycosyltransferase enzyme in fusion with MBP tag at N-term (MBP-GT) in accordance with the present invention.

Figure 2:
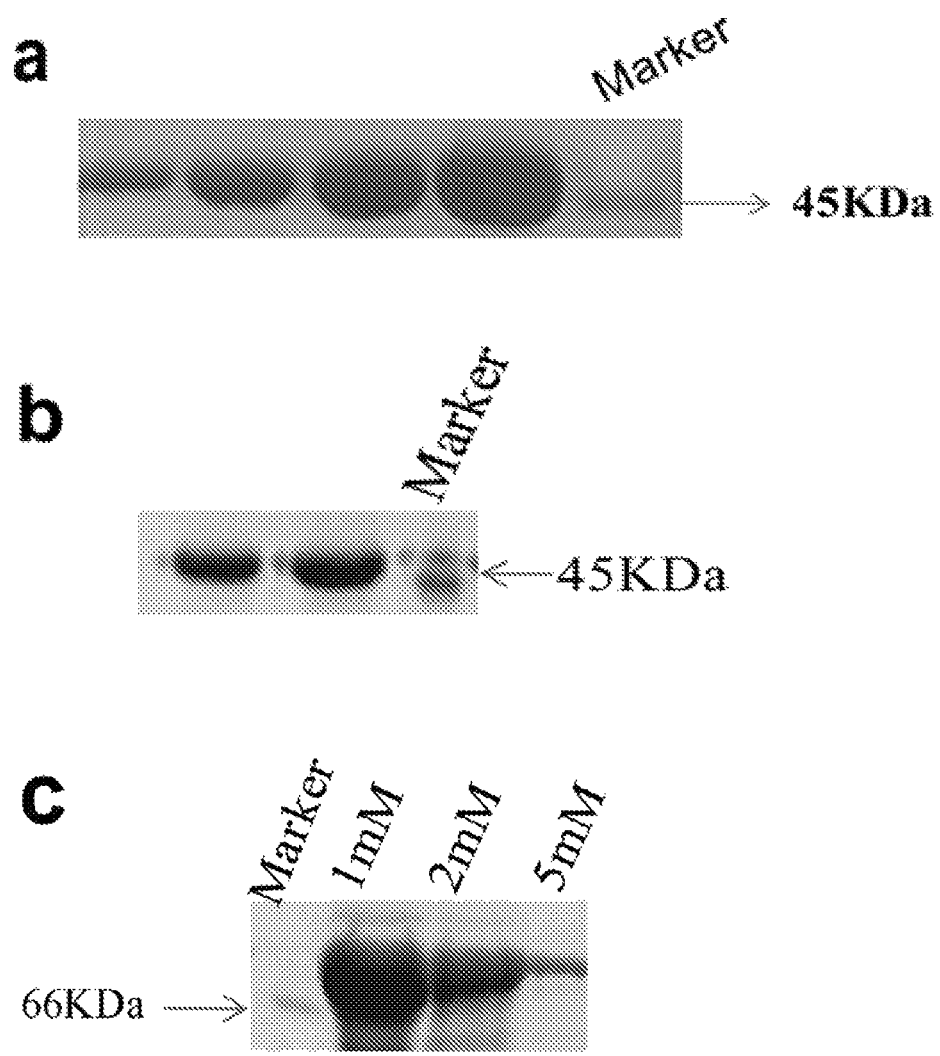
Figure 2:
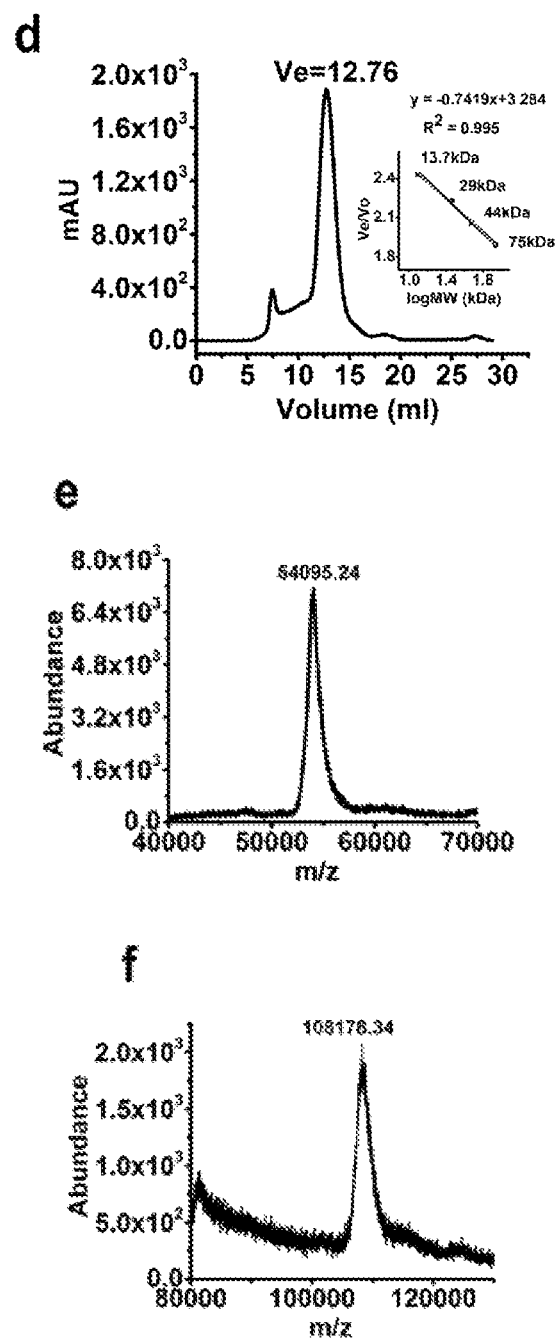

FIG. 2 illustrates the SDS-PAGE profile of purified proteins namely, GT-CTH (Panel a), GT-NTH (Panel b) and MBP-GT (Panel c), Gel filtration profile of purified GT-CTH (Panel d) and MALDI-TOF-MS profile (Panel e-Monomer, Panel f-Dimer) of GT-CTH.

Figure 3:
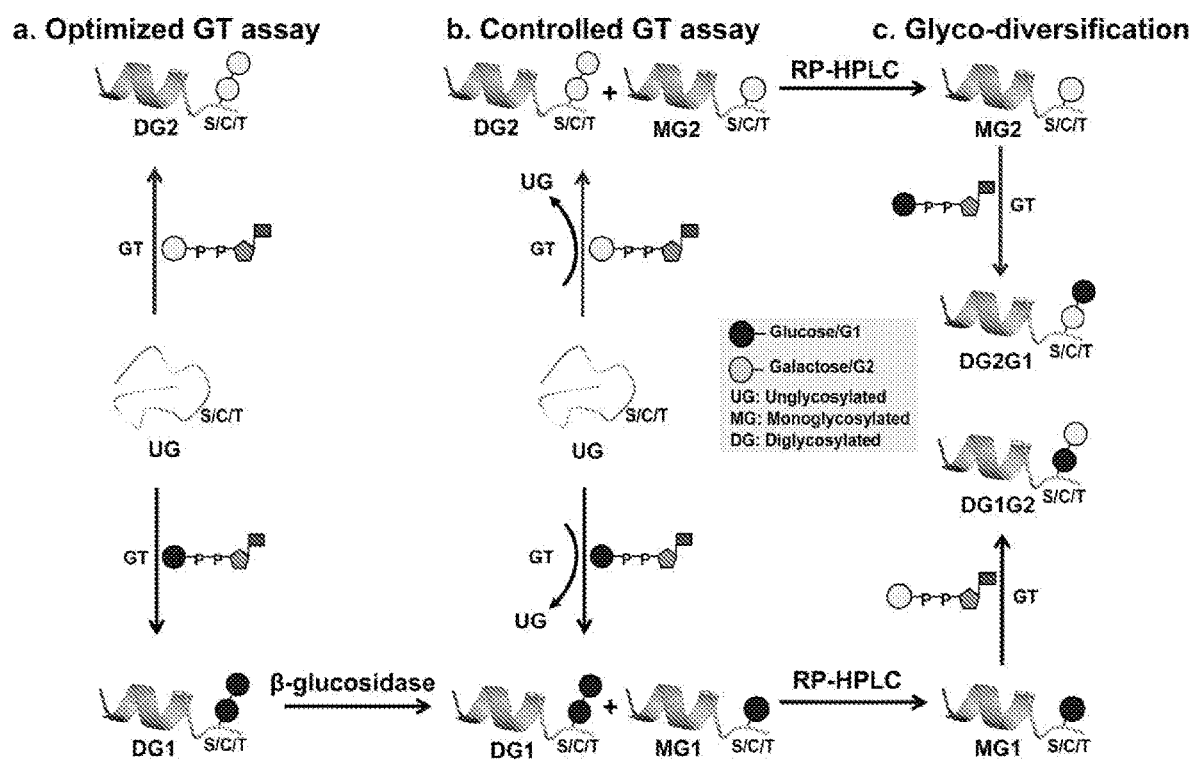

FIG. 3 illustrates the schema of methods of a) optimized GT assay for generating di-glycosylated glycoform of the acceptor substrate according to this invention b) controlled GT assay for generating a mixture of glycoforms of acceptor substrate by modulating enzyme: substrate ratio OR by incubating di-glucosylated product with β-glucosidase (3b-left panel), wherein the β-glucosidase catalyzes the removal of terminal saccharide moiety; c) glyco-diversification of RP-HPLC separated and purified mono-glycosylated glycoform in accordance with the present invention.

DETAILED DESCRIPTION OF THE INVENTION

The present invention relates to a multifunctional recombinant nucleotide dependent glycosyltransferase and methods to glycosylate acceptor substrates in vitro. In particular, the invention relates to nucleotide diphosphate (UDP/GDP) dependent O- and/or S-glycosyltransferase protein from bacteria that catalyzes the transfer of at least two monosaccharides sequentially on to serine or threonine or cysteine residue of an acceptor thereby producing an O-linked and/or S-linked di-glycosylated product.

More particularly, the present invention relates to the ability of the recombinant nucleotide dependent glycosyltransferase to catalyze more than one type of glycosidic linkages and usefulness in one pot synthesis of di-glycosylated product including glycosylated antimicrobial peptide such as enterocin 96, in vitro.

Furthermore, the invention is useful for glyco-diversification of mono-glycosylated glycoforms.

Before the present invention is disclosed and described, it is to be understood that this invention is not limited to the particular process steps and materials disclosed herein, as such process steps and materials may vary to some degree. It is also to be understood that the terminology used herein is used for the purpose of describing particular embodiments only and is not intended to be limiting as the scope of the present invention will be limited only by appended claims and equivalents thereof.

In order to more clearly and concisely describe and point out the subject matter of the claimed invention, the following definitions are provided for specific terms, which are used in the following written description.

The term "Recombinant" when used with reference to a cell indicates that the cell replicates a heterologous nucleic acid (plasmid/vector), or expresses a peptide or protein encoded by a heterologous nucleic acid (recombinant vector/recombinant expression vector). Recombinant cells also contain genes found in the native form of the cell wherein the genes are modified and re-introduced into the cell by artificial means. A "recombinant protein" is the one which has been produced by a recombinant cell.

The terms "Glyco-randomization" and "Glyco-diversification" are used interchangeably herein refer to rapid diversification of bioactive peptides, small molecules, drug leads and/or approved drugs through the attachment of sugars, thereby generating glyco-diversified glycoforms of the same The terms "Bacteriocin" and "Antimicrobial peptides" are used interchangeably herein refer to natural peptides secreted by several bacteria that exert bioactivity against other bacterial species.

The term "Glyco-conjugate" refers to general classification for carbohydrates covalently linked with other chemical species such as proteins, peptides, lipids and saccharides.

The term "Expression" refers to transcription or translation, or both, as context requires.

The term "Nucleotide" refers to a ribonucleotide or a deoxyribonucleotide. "Nucleic acid" refers to a polymer of nucleotides and may be single- or double-stranded. "Polynucleotide" refers to nucleic acid that is twelve or more nucleotides in length.

The term "Donor substrate" with reference to glycosyltransferases, which is an activated nucleotide sugar. Such activated sugars generally consist of uridine, guanosine, and cytidine monophosphate derivatives of the sugars (UMP, GMP and CMP, respectively) or diphosphate derivatives of the sugars (UDP, GDP and CDP, respectively), in which the nucleoside monophosphate or diphosphate serves as a leaving group. For example, a donor substrate for fucosyltransferases is GDP-fucose. Donor substrates for sialyltransferases, for example, are activated sugar nucleotides comprising the desired sialic acid. For instance, in the case of NeuAc, the activated sugar is CMP-NeuAc.

The term "Acceptor substrate" with reference to glycosyltransferase, which is an oligosaccharide, monosaccharides, polypeptides, peptide, lipids, small organic molecules, and even DNA. When the acceptor substrate is contacted with the corresponding glycosyltransferase and sugar donor substrate, and other necessary reaction mixture components, and the reaction mixture is incubated for a sufficient period of time, the glycosyltransferase transfers sugar residues from the sugar donor substrate to the acceptor substrate. The acceptor substrate will often vary for different types of a particular glycosyltransferase.

The term "Product" with reference to glycosyltransferase, which is the glycosylated form of acceptor (oligosaccharide, monosaccharides, polypeptides, peptide, lipids, small organic molecules, and even DNA). When the acceptor substrate is contacted with the corresponding glycosyltransferase and sugar donor substrate, and other necessary reaction mixture components, and the reaction mixture is incubated for a sufficient period of time, the glycosyltransferase transfers sugar residues from the sugar donor substrate to the acceptor substrate thereby generating glycosylated product.

The term "Glycoforms" with reference to acceptor or product, which is differentially glycosylated forms of oligosaccharide, monosaccharides, polypeptides, peptide, lipids, small organic molecules, and even DNA. Such forms differ in nature and or size of glycan attached. Mono-glycosylated and di-glycosylated forms of an un-glycosylated acceptor are the glycoforms of the product.

The term "Glyco-variant" with reference to product, which is glycosylated and glyco-diversified form of acceptor substrate (oligosaccharide, monosaccharides, polypeptides, peptide, lipids, small organic molecules, and even DNA).

In principle, the reaction of the present invention follows the below scheme:

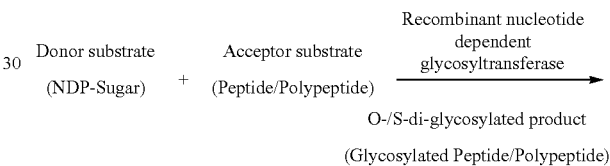

Accordingly, the reaction involves contacting nucleotide dependent glycosyltransferase enzyme with donor substrate and acceptor substrate, wherein the glycosyltransferase catalyzes the transfer of plurality of saccharide moieties from donor substrate to the serine or threonine or cysteine residue in acceptor substrate thereby produces O-linked and/or S-linked di-glycosylated product including glycosylated antimicrobial peptide such as enterocin 96 in vitro.

The donor substrate comprises activated nucleotide sugars such as UDP-glucose, UDP-galactose, UDP-GlcNAc, UDP-glucuronic acid, GDP-mannose, GDP-glucose, GDP-fucose and other related nucleotide sugars thereof. The acceptor substrate corresponds to the peptides or polypeptides with amino acid sequences SEQ ID NO's: (4-17), wherein the acceptor harbors at least one copy of minimal sequon (IHSLLNRLGG(D/E≠G)(S/T/C≠Y/N)(S/T/R/A≠G/D) corresponding to SEQ ID NO: 17 and variants thereof.

One of the aspects of the present invention provides an ability to catalyze transfer of at least two monosaccharide molecules sequentially on to serine or threonine or cysteine residue of an acceptor substrate. Hence, the invention provides one pot synthesis of a disaccharide glycan on to serine or threonine or cysteine residue in acceptor substrate.

Yet another aspect of the present invention provides an ability to catalyze two different linkages in the disaccharide glycan, which includes proximal linkage and terminal linkage. In proximal linkage, serine or threonine or cysteine residue of peptide/polypeptide is defined as O-linked (serine- or threonine-linked) or S-linked (cysteine-linked) to the monosaccharide at proximal/reducing end, whereas anomeric configuration of the linkage is yet undefined. The anomeric configuration of linkage/glycosidic bond between first monosaccharide (at proximal/reducing end) and the second monosaccharide (at terminal/non-reducing end) of the disaccharide glycan is identified as β, which is susceptible to a β-glucosidase. Therefore, the present invention is capable of creating thio-ether linkages (S-linkage) between glycan and acceptor, which are generally more useful and robust than other linkages. Besides, a disaccharide glycan provides more sugar enrichment over monosaccharide glycan through less reaction steps. Such sugar enrichment may affect associated bioactivity of acceptor favorably. Disaccharide glycan also provides longer arm/linker which is more useful for secondary modification. For example; pegylation of glycan in stereo-constrained contexts especially for any bulkier modification.

In addition to polypeptide sequences having multifunctional recombinant nucleotide dependent glycosyltransferase activity, the invention furthermore, provides recombinant DNA molecules (recombinant bacterial expression vectors) encoding proteins having novel glycosyltransferase activities, hybrid vectors comprising such recombinant DNA molecules, recombinant transformed hosts suitable for the multiplication and/or expression of the recombinant DNA molecules The present invention further includes processes for the preparation of the proteins, DNA molecules and hosts.

According to one aspect of the present invention, recombinant bacterial expression vectors carrying the polypeptide sequences of recombinantly expressed nucleotide dependent glycosyltransferase, comprise SEQ ID NO: 1, SEQ ID NO: 2 and SEQ ID NO: 3. The recombinant bacterial expression vectors suitable for expression of multifunctional recombinant nucleotide dependent glycosyltransferase comprise GTpET28a, GTpNIC28-Bsa4 and GTpMAL-c2X, respectively (summarized in Table 1 and FIG. 1). The expression host used here is *Escherichia coli*. Accordingly, the expression of multifunctional recombinant nucleotide dependent glycosyltransferase is optimized in *E. coli* strains, which include *E. coli* Lemo21 (DE3), *E. coli* BL21 (DE3) and *E. coli* Rosetta™ (DE3), respectively.

Hence, the present invention provides an isolated host cell transformed by any of the above described recombinant expression vectors, wherein the cell expresses a protein, polypeptide or peptide of interest encoded by the nucleic acid. In one embodiment, the host cell is a prokaryotic host cell, for example, *Escherichia coli* or a strain thereof.

In yet another aspect, the invention describes the use of acceptor substrate peptides corresponding to SEQ ID NO's: 4, 5, 6, 7, 8, 9, 10, 11, 12, 13, 14, 15, 16, 17 which serve as acceptor substrate for monosaccharide or disaccharide glycan in the presence of multifunctional recombinant nucleotide dependent glycosyltransferase corresponding to SEQ ID NO's: 1, 2 and 3 (Table 2).

Furthermore, the invention provides a minimal acceptor sequon (IHSLLNRLGG(D/E≠G)(S/T/C≠Y/N)(S/T/R/A≠G/D), corresponding to SEQ ID NO: 17 and variants thereof, wherein minimal acceptor sequon is a sequence of consecutive amino acids in a protein that serves as the attachment site to a glycan (monosaccharide or multiples of it linked in various forms). For glycosylation, an acceptor substrate contains at least one exogenous minimal acceptor sequon, but may also includes one or more endogenous (e.g., naturally occurring) minimal acceptor sequon (Table 2).

The present invention is further useful for generating glyco-diversified (di-glycosylated) products as depicted in FIG. 3.

EXAMPLES

In order that this invention is more fully understood the following preparative and testing examples are set forth.

These examples are for the purpose of illustration only and are not to be construed as limiting the scope of the invention in any way.

The below examples describes the cloning, expression and purification of multifunctional recombinant nucleotide dependent glycosyltransferase, optimized and controlled methods for in vitro glycosylation, method for separation and purification of product glycoforms, method for glyco-diversification, assessment of differential bioactivity of glycoforms of enterocin 96 peptide, a known antimicrobial peptide.

Example 1

1.1 Construction of Recombinant Nucleotide Dependent Glycosyltransferase Expression Vector The DNA sequence of nucleotide dependent glycosyltransferase gene (locus NZ_GG668924/EntS) termed GT gene hereafter, is retrieved from NCBI and the gene is custom synthesized and obtained from Genscript. The gene is custom synthesized using pUC57 vector between Nco1 and Xho1 restriction sites. The gene is sub-cloned into pET28a vector in order to get a C-terminal 6×-His tagged recombinant protein. Further, pUC57 plasmid containing GT gene and pET28a plasmid are amplified and double digested using Nco1 and Xho1 to prepare insert DNA fragment and cloning vector, respectively. Both the digests are then further gel extracted using NucleoSpin extract II (Macherey-Nagel, Germany). The purified products are then ligated using T4 DNA ligase. The ligation mixture is then transformed into *E. coli* TOP10 (Invitrogen) cells using heat shock and cells are plated on LB-kanamycin agar plate and grown for 12 h at 37° C. Following incubation for 12 h at temperature 37° C., several colonies are screened using colony PCR and positive colonies are inoculated into LB broth and plasmid isolation is done using Miniprep kit (Qiagen). The successful transformants/clones are then confirmed by double digestion of isolated recombinant plasmid/vector named GTpET28a using Nco1 and Xho1 and the sequence of resulting recombinant plasmid/vector harbored in transformant is confirmed by DNA sequencing.

Further, GT gene is subcloned into pNIC28-Bsa4 vector between Nco1 and Xho1 sites in order to get N-terminal 6×-His tagged recombinant nucleotide dependent glycosyltransferase (GT-NTH). Besides GT gene is subcloned into pMAL-c2X vector between Nde1 and Xho1 restriction sites in order to get N-terminal MBP tagged recombinant nucleotide dependent glycosyltransferase (MBP-GT). Hence, the above cloning is carried out using GTpET28a recombinant plasmid as template. FIG. 1 illustrates the vector maps of bacterial protein expression vectors encoding recombinant nucleotide dependent glycosyltransferase, in accordance with the present invention.

1.2 Over Expression and Purification of His-Tagged Recombinant Nucleotide Dependent Glycosyltransferase (GT-CTH and GT-NTH)

The *E. coli* Lemo21 (DE3) (NEB) cells are transformed with GTpET28a construct using heat shock. A single colony is inoculated into 30 ml LB broth containing 50 µg/ml kanamycin and 35 µg/ml chloramphenicol. The primary culture is grown overnight at 37° C. and used to inoculate 3 L LB broth containing 50 µg/ml kanamycin, 35 µg/ml chloramphenicol and 25 µM L-Rhamnose. The culture is then grown at 37° C. to $OD_{600}$~0.6. Further, the culture is induced using 0.4 mM IPTG and incubated at 25° C. for 12 h. Cells are then harvested at 8000×rpm for 20 min at 4° C.

The construct GTpNIC-Bsa4 is transformed into *E. coli* BL21 (DE3) (NEB) for over expression wherein a single colony is inoculated into 30 ml LB broth containing 50 µg/ml kanamycin. The primary culture is grown overnight at 37° C. and used to inoculate 3 L LB broth. The culture is then grown at 37° C. to $OD_{600}$~0.6. Further, the culture is induced using 0.5 mM IPTG and incubated at 18° C. for 16 h. Cells are then harvested at 8000×rpm for 20 min at 4° C.

After expression the cell pellet (GT-CTH/GT-NTH) is resuspended in 150 ml of start buffer (20 mM HEPES, pH 7.5, 500 mM NaCl, 2 mM DTT and 10% Glycerol) and cell lysis is carried out using sonication with 10 sec on and 10 sec off pulse and 25% amplitude. The cell debris is then removed by centrifuging at 12000×rpm for 30 min at 4° C. The supernatant is further subjected to metal affinity chromatography.

The supernatant is left for binding with Ni-sepharose beads previously washed and equilibrated with start buffer. The binding time is 15 min. Flow through is collected and bound beads are washed with washing buffer (20 mM HEPES, pH 7.5, 1 M NaCl, 2 mM DTT, 30 mM imidazole, 10% glycerol). The salt concentration in washing buffer is gradually reduced upto 200 mM and elution is done with half column volume of elution buffer (20 mM HEPES, pH 7.5, 200 mM imidazole, 200 mM NaCl, 2 mM DTT). The fractions containing desired protein are pooled and concentrated using Amicon ultra membrane filters (30 KDa MWCO, Millipore). The desired protein is then further subjected to gel filtration chromatography. The concentrated protein sample is injected onto a FPLC system (AKTA, GE Healthcare life sciences) equipped with Superdex-200 10/300 GL (GE Healthcare life sciences) previously equilibrated with 20 mM HEPES, pH 7.5, 200 mM NaCl and 2 mM DTT. The elution is done at a flow rate of 0.5 ml/min and monitored at 280 nm. The desired fractions are then collected, pooled and concentrated using Amicon ultra membrane filters (30 KDa MWCO, Millipore). The concentration is estimated using Bradford reagent and protein is stored at −80° C. wherein the yield generated is approximately 12-15 mg of protein from 3 L culture.

1.3 Over Expression and Purification of MBP Tagged Recombinant Nucleotide Dependent Glycosyltransferase (MBP-GT)

The construct GTpMAL-c2x is transformed into *E. coli* Rosetta™ (DE3) cells and for purification a single colony is inoculated into 30 ml LB broth containing 100 µ/ml ampicillin and 35 µg/ml chloramphenicol. The primary culture is grown overnight at 37° C. and used to inoculate 3 L LB broth containing 100 µg/ml ampicillin, 35 µg/ml chloramphenicol and 0.2% D-glucose. The culture is then grown at 37° C. to $OD_{600}$~0.6. Further, the culture is induced using 0.5 mM IPTG and incubated at 18° C. for 16 h. Cells are harvested at 8000×rpm for 20 min at 4° C. The cell lysate is left for binding with amylose resin previously washed and equilibrated with lysis buffer (20 mM HEPES, pH 7.5, 500 mM NaCl, 10 mM β-ME and 10% glycerol). The binding time is 1 h. Flow through is collected and bound beads are washed with washing buffer (20 mM HEPES, pH 7.5, 200 mM NaCl, 1 mM DTT). Further, the elution is done using elution buffer (20 mM HEPES, pH 7.5, 200 mM NaCl, 1 mM DTT) containing gradually increasing concentrations of maltose (1 mM, 2 mM, 5 mM, 10 mM). The fractions containing desired protein are pooled and concentrated using Amicon ultra membrane filters (30 KDa MWCO, Millipore). The desired protein is then further subjected to gel filtration chromatography using the above mentioned protocol.

FIG. 2 illustrates the purification profile of various fusions of recombinant nucleotide dependent glycosyltransferase enzyme as described above. Panel a, Panel b and Panel c illustrate the SDS-PAGE profile of GT-CTH, GT-NTH and MBP-GT (in the presence of different concentrations of maltose i.e. 1 mM, 2 mM and 5 mM), with corresponding protein bands visible at 54.1 KDa, 55.6 KDa and 93.8 KDa, respectively; Panel d illustrates the gel filtration profile of GT-CTH protein where Ve=12.76 (Ve/Vo=1.77), Expected MW=54156 Da, Observed MW=108600 Da, suggesting that purified recombinant nucleotide dependent glycosyltransferase elutes as dimer; Panel e and Panel f illustrate the results of MALDI-TOF-MS profile of purified GT-CTH containing monomer (Observed mass 54095.24 Da, Expected mass 54156.80 Da) and dimer (Observed mass 108178.34 Da, Expected mass 108313.60 Da), respectively.

TABLE 1

| | Name of the Recombinant Expression Vector | | |
|---|---|---|---|
| | GTpET28a | GTpNIC28-Bsa4 | GTpMAL-c2X |
| Restriction sites used for cloning | NcoI-XhoI | NcoI-XhoI | NdeI-XhoI |
| Name of the Recombinant Protein (Nucleotide dependent glycosyltransferase) | GT-CTH | GT-NTH | MBP-GT |
| Fusion/Purification tag | C-terminal His tag | N-terminal His tag | N terminal MBP tag |
| In vivo Expression status | Soluble | Soluble | Soluble |
| Optimum Prokaryotic host for Expression | *E. coli* Lemo21(DE3) (NEB #C2528) | *E. coli* BL21(DE3) (NEB# C2527I) | *E. coli* Rosetta™ (DE3) (Novagen #70954) |

Example 2

2.1 Method for In Vitro Glycosylation of Acceptor Substrate Using Purified GT-CTH Enzyme (Providing Optimized Glycosyltransferase Assay/Optimized GT Assay Conditions)

Purified recombinant nucleotide dependent glycosyltransferase (0.2 µM) is incubated with synthetic acceptor substrates (5 µM) and 100 µM UDP-glucose in a reaction buffer containing 20 mM HEPES, pH 7.5, 50 mM NaCl, 1 mM TCEP and 1 mM $MgCl_2$. The reaction is incubated at 25° C. for 12 h. Each assay reaction was accompanied by control reaction (without enzyme). The reactions are quenched with 5% TFA to pH 2, desalted using ZipTip $C_{18}$, and vacuum dried and analyzed using mass spectrometry.

2.2 Method for Detecting Glycosylated Products (Providing Optimized Method) Using Mass Spectrometry Mass spectrometry has been used to detect glycosylation in product of glycosylation assay reactions using Matrix Assisted Laser Desorption Ionization Time of flight mass spectrometry (MALDI-TOF MS) and Liquid chromatography electrospray ionization mass spectrometry (LC/ESI-MS) techniques. MALDI-TOF MS has carried out at AB Sciex 5800 MALDI TOF/TOF and LC/ESI-MS has carried out at 6550 iFunnel QTOF LC/MS (Agilent Technologies) using Zorbax Eclipse plus C8 column (3.0×150 mm, 5µ) of Agilent technologies. For MALDI-TOF analysis and LC-ESI/MS analysis, vacuum dried samples are reconstituted in water and 0.1% formic acid respectively.

2.3 Acquisition and Analysis of MALDI-TOF Spectra

Prior to sample data acquisition, the analyzer was externally calibrated using a mixture of the peptides, angiotensin, bradykinin, Glu-1-Fibrinopeptide, ACTH fragment 1-17, ACTH fragment 18-39, and ACTH fragment 7-38 (Part No: 4333604, AB Sciex). For MALDI-TOF MS analysis of salt-free samples, 1 µL aliquot of analyte is combined with 1 µL of matrix (α-cyano-4-hydroxy-cinnamic acid matrix in 50% ACN/50% water with 0.1% TFA) and the total volume is spotted onto a 384 well MALDI target plate and dried under ambient conditions prior to analysis. MS data acquisition is done in reflector and positive ion mode using laser intensity in the range of 3000-3400 V, keeping the mass range 400-700 Da, total number of shots 2000, bin size 0.5 ns and pulse rate 400 Hz. Further MSMS data was collected in mass range 10-4000 Da keeping the laser intensity in range of 4000-4200 V and adduct tolerance 0.03. Precursors having S/N and resolution below 20 and 200 respectively were excluded for MSMS. Post-acquisition, the raw data was extracted in the format of t2d files, imported in the Data Explorer software, version 4.9 of Applied Biosystems and converted in to text file format. The text files having the peaks list, imported and plotted in Origin (OriginPro 2015 b.9.2.214).

2.4 Acquisition and Analysis of LC-ESI-Q/TOF Spectra

A 5 µL volume of sample is injected on Agilent UPLC system equipped with C8 column equilibrated in 40% B (solvent A=0.1% formic acid in water, solvent B=0.1% formic in acetonitrile). The sample is then fractionated by employing a gradient of solvent B (40%-100%) over 12 min with 0.4 ml/min flow rate and directly subjected to ESI-Q/TOF MS. Data is acquired in Dual AJS ESI positive ion mode with the capillary voltage set to 4.5 kV. Nitrogen is used as sheath gas (11 L/min). The ionization source and sheath gas are heated to 200° C. and 300° C., respectively. Nozzle and fragmentor voltage are kept at 1000V and 280V, respectively.

MassHunter workstation software, version B.05.00 by Agilent Technologies was used for data acquisition. Post-acquisition, the acquired raw data (.d files) were imported into MassHunter qualitative analysis software, version B.05.00 for further processing. The expected multiple charged ions of the peptides were observed between 2.5-3.5 minutes of retention time in the acquired LC chromatogram (TIC). The TIC corresponding to the expected multiple charged ions was integrated and deconvoluted to obtain MS spectrum and plotted in Origin (OriginPro 2015 b.9.2.214).

In accordance with the present invention, the acceptor substrate having SEQ ID NO: 4 was incubated with recombinant nucleotide dependent glycosyltransferase in the presence of UDP-glucose and MgCl$_2$. The reaction was then analyzed using LC-ESI-Q/TOF, which showed observed average mass of di-glycosylated product as 5503.47 Da (Expected average mass 5503.00 Da) and observed average mass of un-glycosylated product as 5179.70 Da, (Expected average mass 5179.00 Da).

In accordance with the present invention, the acceptor substrate having SEQ ID NO: 9 was incubated with recombinant nucleotide dependent glycosyltransferase in presence of UDP-glucose and MgCl$_2$. The reaction was then analyzed using MALDI-TOF, which showed observed (M+H)$^+$ of di-glycosylated product as 2424.65 Da (Expected (M+H)$^+$ 2424.07 Da) and observed (M+H)$^+$ of mono-glycosylated product as 2262.57 Da (Expected (M+H)$^+$ 2262.07 Da) and observed (M+H)$^+$ of un-glycosylated product as 2100.49 Da (Expected (M+H)$^+$ 2100.07 Da).

In accordance with the present invention, the acceptor substrate having SEQ ID NO: 5 was incubated with recombinant nucleotide dependent glycosyltransferase in presence of UDP-glucose and MgCl$_2$. The reaction was then analyzed using LC-ESI-Q/TOF, which showed observed monoisotopic mass of di-glycosylated product as 5515.53 Da (Expected monoisotopic mass 5515.41 Da) and observed monoisotopic mass of un-glycosylated product as 5190.91 Da (Expected monoisotopic mass 5191.41 Da).

2.5 Identification of Glycosylated Residues in Glycosylated Products Using Mass Spectrometry 2.5a chymotrypsin digestion of acceptor and product: For glycosite annotation the glycosylated and their respective un-glycosylated acceptor are digested using chymotrypsin (Sigma) in presence of 100 mM Tris-Cl, pH 7.5, 10 mM CaCl$_2$ 5 mM TCEP. The reactions are incubated at 30° C. for 5 h and quenched with 5% TFA to pH 2. The reactions are then desalted using ZipTip C$_{18}$ and vacuum dried. For MALDI-TOF-MS and tandem MS analysis, the samples are reconstituted in water. Further the MS/MS is carried out for all the peaks of interest.

2.5b MALDI-TOF-MS and tandem MS spectra analysis of chymotrypsin digested products: MALDI-TOF-MS and tandem MS spectra of chymotrypsin digested products are acquired using the above mentioned method of acquisition and analysis of MALDI-TOF spectra. Tandem MS is performed of all the peaks of interest and the glycosylated residue is identified by manual de novo peptide sequencing.

In accordance with the present invention, the acceptor substrates having SEQ ID NO: 4, SEQ ID NO: 9 and SEQ ID NO: 5 were in vitro glycosylated using recombinant nucleotide dependent glycosyltransferase, chymotrypsin digested and analyzed on MALDI-TOF. The resulting MSMS spectrum of 2774.39 Da peak of acceptor substrate corresponding to SEQ ID NO: 4 identified serine at 33 position to be the glycosite. The resulting MSMS spectrum of 2424.65 Da peak corresponding to SEQ ID NO: 9 identified threonine at 33 position to be the glycosite. The resulting MSMS spectrum of 2790.39 Da peak corresponding to SEQ ID NO: 5 identified cysteine at 33 position to be the glycosite.

Example 3

3.1 Method of Controlled GT Assay to Generate a Mixture of Glycoforms of Product The GT assay conditions were optimized to get a mixture of un-glycosylated, mono-glycosylated and di-glycoyslated products. 100 µM acceptor peptide (SEQ ID NO: 4) was incubated with 0.25 µM recombinant nucleotide dependent glycosyltransferase (keeping [E]:[S]=1:400) and 100 µM UDP-glucose/UDP-galactose in presence of reaction buffer containing 20 mM HEPES, pH 7.5, 50 mM NaCl, 1 mM TCEP and 0.5 mM MgCl$_2$ for 1 h at 25° C. FIG. 3b illustrates the schema of generating a mixture of un-glycosylated, mono-glycosylated and di-glycoyslated products by incubating the acceptor substrate, donor substrate and recombinant nucleotide dependent glycosyltransferase under controlled GT assay conditions.

3.2 Method of Generating a Mixture of Glycoforms of Di-Glycosylated Product Using Exoglycosidase.

The di-glucosylated product (SEQ ID NO: 4) is deglycosylated using suitable exoglycosidase (β-glucosidase). The acceptor substrate is first di-glucosylated under aforesaid optimized GT assay conditions and the di-glucosylated product (5 μM) is incubated with 2 μg/μL of β-glucosidase (Catalogue No: 195197, MP Biomedicals) in reaction buffer containing 100 mM sodium acetate buffer, pH 5.0 and 1× purified BSA for 18 h. The control reaction is carried out by incubating all reaction components in absence of β-glucosidase. LC-ESI-Q-TOF MS analysis of β-glucosidase treated product shows the mixture of di-glucosylated and monoglucosylated forms. FIG. 3b (left panel) illustrates schema for deglycosylation of di-glucosylated product (SEQ ID NO: 4) in accordance with the present invention. The di-glucosylated product was incubated with β-glucosidase and the reaction was then analyzed using LC-ESI-Q/TOF, which showed that major population of di-glucosylated product (Observed average mass 5500.12 Da) is converted in to mono-glucosylated product (Observed average mass 5337.42 Da).

3.3 Method of Separation and Purification of Glycoforms of Product:

The reactions are analyzed on analytical HPLC system (Shimadzu) using a reverse phase column of Phenomenex (Jupitor 5 μm C18 column, 250×4.6 mm, 300 Å) and RP-HPLC method is optimized to separate the mixture of un-glycosylated, mono-glycosylated and di-glycosylated products. 20 μL of the reaction mixture is injected on the column previously equilibrated with 5% solvent B (solvent A: 0.1% TFA in water, solvent B: 0.1% TFA in ACN). The sample is fractionated by employing a gradient of solvent B (5-100%) over 26 min with a flow rate of 1 ml/min and observed at wavelength of 220 nm. The masses of separated glycoforms are further checked by MALDI-TOF-MS, which confirms that di-glycosylated product elutes first, followed by mono-glycosylated and then un-glycosylated product. The purified HPLC fractions containing single species are lyophilized and stored at −80° C. The similarly separation can also be achieved for species obtained upon exoglycosidase treatment of di-glycosylated product as stated further.

3.4 Method for Glyco-Diversification of Purified Mono-Glycosylated Form of Product The RP-HPLC purified mono-glucosylated product is glyco-diversified using UDP-galactose and recombinant nucleotide dependent glycosyltransferase under controlled GT assay conditions. Similarly, mono-galactosylated product is glyco-diversified using UDP-glucose and recombinant nucleotide dependent glycosyltransferase under controlled GT assay conditions. The masses of all glyco-diversified products are confirmed by MALDI-TOF-MS. FIG. 3c illustrates the approach used for glyco-diversification of acceptor substrate in accordance with the present invention.

Example 4

Assessment of Differential Bioactivity of Glycoforms of Enetrocin 96 Peptide, a Known Antimicrobial Peptide The di-glycosylated, mono-glycosylated and un-glycosylated glycoforms corresponding to enterocin 96 (known bacteriocin) peptide sequence are prepared under controlled GT assay conditions and purified using RP-HPLC based method. The lyophilized product glycoforms including glyco-diversified forms are resuspended in 50 mM Tris-Cl, pH 7.5. The culture of *Listeria monocytogenes* EGD-e is grown in BHI media at 37° C. for 7-8 h. Agar plates are prepared by mixing 25 μL of saturated culture ($A_{600}$≈1.5) and 100 mL of molten BHI agar (cooled to 40-45° C.) and pouring the mixture into sterile petri plates. The seeded agar plates are allowed to solidify for 30-45 min and agar wells are prepared using a sterile cork borer. 50 μM of all glycoforms including glyco-diversified forms are poured in to the wells and plates are incubated at 37° C. for 12 h. The antimicrobial activity is determined by the presence and absence of zone of growth inhibition.

The bioactivity of glycoforms corresponding to SEQ ID NO: 4 in accordance with the present invention were checked against *Listeria monocytogenes* EGD-e where di-glucosylated product showed more antimicrobial activity than mono-glucosylated product. Mono-galactosylated product and glyco-diversified form where glucose was at proximal and galactose was at terminal position did not show bioactivity, whereas the glyco-diversified form where galactose was at proximal and glucose was at terminal position showed bioactivity.

Example 5

Identification of Minimal Acceptor Sequon

In order to identify the minimal acceptor sequence, various acceptor substrates (SEQ ID NO: 4-SEQ ID NO: 17) mentioned in Table 2 are analyzed using the above mentioned methods. The IHSLLNRLGG(D/E≠G)(S/T/C≠Y/N)(S/T/R/A≠G/D) corresponding to SEQ ID NO: 17 and variants thereof is found to be optimum as minimal acceptor sequon.

TABLE 2

| Name | Role | Sequence (N→C) |
|---|---|---|
| SEQ ID NO: 1 | Encodes C-terminal 6X-His tagged recombinant nucleotide dependent Glycosyltransferase protein (GT-CTH) | MGYSENFIANDWENVEVENKNKYTLTNQENKDVTELWLQILKG LKFPNELKETVSYSKNLKELSLKTHAEVSVCIIAKNEQDSIRK CINSIYEFSDEIIFIDTGSIDSTKKIVKEIASEKVKIFDYTWQ DDFSDARNYSIQKASKEWILIIDADEYVSSDELIKLRLLIDML DRFKFKDSLRVSCAIYQLDNVITHGQSRLFRNNNKIKYYGLIH EELRNNKGLDPIFNVESEITFFHDGYKEILRKEKCERNIRLLA KMLEKEPDNVRWAYLYCRDSFSINSNIDFEKILLPFLIKNMDE SISCENILLTNYTHLILFLITKKYIIDGKSSLASKCIEVLEKM LPNSSDVTFYKFLNKQHSLYEQQFEFLKEVIQFRKNNEYDQYS QIGCNLLHYDLLISGLLFDVKSYDYSYQYFLKLDLANYFSELE IPDEYKMLINKYRENESLEHHHHHH |
| SEQ ID NO: 2 | Encodes N-terminal 6X-His tagged recombinant nucleotide | MHHHHHHSSGVDLGTENLYFQSMGYSENFIANDWFNVEVFNKN KYTLTNQENKDVTELWLQILKGLKFPNELKETVSYSKNLKELS LKTHAEVSVCIIAKNEQDSIRKCINSIYEFSDEIIFIDTGSID STKKIVKEIASEKVKIFDYTWQDDFSDARNYSIQKASKEWILI IDADEYVSSDELIKLRLLIDMLDRFKFKDSLRVSCAIYQLDNV |

TABLE 2-continued

| Name | Role | Sequence (N→C) |
|---|---|---|
| | dependent Glycosyltransferase protein (GT-NTH) | ITHGQSRLFRNNNKIKYYGLIHEELRNNKGLDPIFNVESEITF FHDGYKEILRKEKCERNIRLLAKMLEKEPDNVRWAYLYCRDSF SINSNIDFEKILLPFLIKNMDESISCENILLTNYTHLILFLIT KKYIIDGKSSLASKCIEVLEKMLPNSSDVTFYKFLNKQHSLYE QQFEFLKEVIQFRKNNEYDQYSQIGCNLLHYDLLISGLLFDVK SYDYSYQYFLKLDLANYFSELEIPDEYKMLINKYRENES |
| SEQ ID NO: 3 | Encodes N-terminal MBP tagged recombinant nucleotide dependent Glycosyltransferase fusion protein (MBP-GT) | MKIEEGKLVIWINGDKGYNGLAEVGKKFEKDTGIKVTVEHPDK LEEKFPQVAATGDGPDIIFWAHDRFGGYAQSGLLAEITPDKAF QDKLYPFTWDAVRYNGKLIAYPIAVEALSLIYNKDLLPNPPKT WEEIPALDKELKAKGKSALMFNLQEPYFTWPLIAADGGYAFKY ENGKYDIKDVGVDNAGAKAGLTFLVDLIKNKHMNADTDYSIAE AAFNKGETAMTINGPWAWSNIDTSKVNYGVTVLPTFKGQPSKP FVGVLSAGINAASPNKELAKEFLENYLLTDEGLEAVNKDKPLG AVALKSYEEELAKDPRIAATMENAQKGEIMPNIPQMSAFWYAV RTAVINAASGRQTVDEALAAAQTNAAHMYSENFIANDWFNVEV FNKNKYTLTNQENKDVTELWLQILKGLKFPNELKETVSYSKNL KELSLKTHAEVSVCIIAKNEQDSIRKCINSIYEFSDEIIFIDT GSIDSTKKIVKEIASEKVKIFDYTWQDDFSDARNYSIQKASKE WILIIDADEYVSSDELIKLRLLIDMLDRFKFKDSLRVSCAIYQ LDNVITHGQSRLFRNNNKIKYYGLIHEELRNNKGLDPIFNVES EITFFHDGYKEILRKEKCERNIRLLAKMLEKEPDNVRWAYLYC RDSFSINSNIDFEKILLPFLIKNMDESISCENILLTNYTHLIL FLITKKYIIDGKSSLASKCIEVLEKMLPNSSDVTFYKFLNKQH SLYEQQFEFLKEVIQFRKNNEYDQYSQIGCNLLHYDLLISGLL FDVKSYDYSYQYFLKLDLANYFSELEIPDEYKMLINKYRENES LE |
| SEQ ID NO: 4 | Acceptor substrate 1 | MSKRDCNLMKACCAGQAVTYAIHSLLNRLGGDSSDPAGCNDIV RKYCK |
| SEQ ID NO: 5 | Acceptor substrate 2 | MSKRDCNLMKACCAGQAVTYAIHSLLNRLGGDCSDPAGCNDIV RKYCK |
| SEQ ID NO: 6 | Acceptor substrate 3 | MSKRDCNLMKACCAGQAVTYAIHSLLNRLGGDSSDP |
| SEQ ID NO: 7 | Acceptor substrate 4 | AVTYAIHSLLNRLGGDSSDPAGCNDIVRKYCK |
| SEQ ID NO: 8 | Acceptor substrate 5 | AVTYAIHSLLNRLGGDSSDP |
| SEQ ID NO: 9 | Acceptor substrate 6 | AVTYAIHSLLNRLGGDTSDP |
| SEQ ID NO: 10 | Acceptor substrate 7 | AVTYAIHSLLNRLGGESSDP |
| SEQ ID NO: 11 | Acceptor substrate 8 | AVTYAIHSLLNRLGGDSAP |
| SEQ ID NO: 12 | Acceptor substrate 9 | AVTYAIHSLLNRLGGDSSP |
| SEQ ID NO: 13 | Acceptor substrate 10 | AVTYAIHSLLNRLGGDSRP |
| SEQ ID NO: 14 | Acceptor substrate 11 | AVTYAIHSLLNRLGGDSTP |
| SEQ ID NO: 15 | Acceptor substrate 12 | AVTYAIHSLLNRLGGDSS |
| SEQ ID NO: 16 | Acceptor substrate 13 | AIHSLLNRLGGDSSDP |
| SEQ ID NO: 17 | Acceptor substrate 14 | IHSLLNRLGGDSSDP |
| SEQ ID NO: 18 | Expression cassette encoding GT-CTH | CATGGGCTATTCTGAAAATTTTATTGCTAATGACTGGTTTAAT GTAGAGGTATTTAATAAAAATAAGTATACTTTAACGAACCAAG AGAATAAAGATGTAACAGAATTATGGTTACAAATTTTAAAAGG GCTAAAGTTCCCCAACGAATTAAAGGAAACTGTCAGTTACTCT AAAAATTTAAAAGAATTATCTTTAAAAACTCACGCAGAAGTAT CTGTATGTATTATTGCTAAGAATGAACAGGATTCAATAAGAAA ATGTATTAATAGTATCTATGAATTTTCAGATGAAATTATATTT ATTGATACAGGATCAATTGATTCGACAAAAAAAATAGTAAAAG |

TABLE 2-continued

| Name | Role | Sequence (N→C) |
|---|---|---|
| | | AAATAGCAAGCGAAAAAGTAAAAATATTTGATTATACTTGGCA
AGATGATTTTTCAGATGCGAGAAATTATTCAATACAAAAAGCA
AGTAAAGAATGGATATTAATTATTGATGCAGATGAATATGTAT
CTTCAGATGAGCTTATCAAATTAAGGCTCTTAATAGATATGTT
AGACAGGTTTAAATTTAAAGATTCATTAAGAGTTAGTTGTGCA
ATATATCAATTAGATAATGTTATCACACATGGCCAAAGTCGAT
TATTTAGAAACAATAATAAAATTAAGTATTATGGTCTAATACA
TGAAGAGTTGAGGAACAACAAAGGATTAGATCCAATTTTTAAC
GTTGAAAGTGAGATTACTTTTTTCCATGACGGTTACAAAGAAA
TACTTAGGAAAGAGAAGTGTGAAAGAAACATAAGGCTACTAGC
TAAGATGTTAGAAAAAGAGCCAGACAATGTTAGATGGGCATAC
TTGTATTGTAGAGATTCATTTTCTATAAATTCCAACATTGATT
TTGAAAAAATTCTACTTCCATTTTTAATAAAGAATATGGATGA
AAGTATATCATGTGAGAATATCCTACTTACAAACTATACTCAT
TTAATCCTATTTCTTATTACTAAGAAATATATAATTGATGGGA
AAAGCTCACTTGCAAGTAAATGTATAGAGGTGTTAGAAAAAAT
GCTACCTAACTCTTCTGATGTTACTTTTTACAAATTTTTAAAT
AAACAGCATAGTTTGTATGAACAACAATTTGAATTTTTAAAAG
AAGTAATTCAATTTAGAAAAAATAATGAATATGATCAATATAG
CCAAATAGGGTGTAATTTATTACACTATGATTTATTAATTTCA
GGATTACTTTTTGATGTTAAGTCTTATGATTATTCATATCAAT
ACTTTTTAAAATTAGATTTAGCTAACTATTTTTCTGAATTAGA
GATTCCTGATGAATACAAAATGTTAATAAATAAGTATCGGGAG
AATGAATCAC |
| SEQ ID NO: 19 | Expression cassette encoding GT-NTH | CATGGGCTATTCTGAAAATTTTATTGCTAATGACTGGTTTAAT
GTAGAGGTATTTAATAAAAATAAGTATACTTTAACGAACCAAG
AGAATAAAGATGTAACAGAATTATGGTTACAAATTTTAAAAGG
GCTAAAGTTCCCCAACGAATTAAAGGAAACTGTCAGTTACTCT
AAAAATTTAAAAGAATTATCTTTAAAAACTCACGCAGAAGTAT
CTGTATGTATTATTGCTAAGAATGAACAGGATTCAATAAGAAA
ATGTATTAATAGTATCTATGAATTTTCAGATGAAATTATATTT
ATTGATACAGGATCAATTGATTCGACAAAAAAAATAGTAAAAG
AAATAGCAAGCGAAAAGTAAAAATATTTGATTATACTTGGCA
AGATGATTTTTCAGATGCGAGAAATTATTCAATACAAAAAGCA
AGTAAAGAATGGATATTAATTATTGATGCAGATGAATATGTAT
CTTCAGATGAGCTTATCAAATTAAGGCTCTTAATAGATATGTT
AGACAGGTTTAAATTTAAAGATTCATTAAGAGTTAGTTGTGCA
ATATATCAATTAGATAATGTTATCACACATGGCCAAAGTCGAT
TATTTAGAAACAATAATAAAATTAAGTATTATGGTCTAATACA
TGAAGAGTTGAGGAACAACAAAGGATTAGATCCAATTTTTAAC
GTTGAAAGTGAGATTACTTTTTTCCATGACGGTTACAAAGAAA
TACTTAGGAAAGAGAAGTGTGAAAGAAACATAAGGCTACTAGC
TAAGATGTTAGAAAAAGAGCCAGACAATGTTAGATGGGCATAC
TTGTATTGTAGAGATTCATTTTCTATAAATTCCAACATTGATT
TTGAAAAAATTCTACTTCCATTTTTAATAAAGAATATGGATGA
AAGTATATCATGTGAGAATATCCTACTTACAAACTATACTCAT
TTAATCCTATTTCTTATTACTAAGAAATATATAATTGATGGGA
AAAGCTCACTTGCAAGTAAATGTATAGAGGTGTTAGAAAAAAT
GCTACCTAACTCTTCTGATGTTACTTTTTACAAATTTTTAAAT
AAACAGCATAGTTTGTATGAACAACAATTTGAATTTTTAAAAG
AAGTAATTCAATTTAGAAAAAATAATGAATATGATCAATATAG
CCAAATAGGGTGTAATTTATTACACTATGATTTATTAATTTCA
GGATTACTTTTTGATGTTAAGTCTTATGATTATTCATATCAAT
ACTTTTTAAAATTAGATTTAGCTAACTATTTTTCTGAATTAGA
GATTCCTGATGAATACAAAATGTTAATAAATAAGTATCGGGAG
AATGAATCATGAC |
| SEQ ID NO: 20 | Expression cassette encoding MBP-GT | TATGTATTCTGAAAATTTTATTGCTAATGACTGGTTTAATGTA
GAGGTATTTAATAAAAATAAGTATACTTTAACGAACCAAGAGA
ATAAAGATGTAACAGAATTATGGTTACAAATTTTAAAAGGGCT
AAAGTTCCCCAACGAATTAAAGGAAACTGTCAGTTACTCTAAA
AATTTAAAAGAATTATCTTTAAAAACTCACGCAGAAGTATCTG
TATGTATTATTGCTAAGAATGAACAGGATTCAATAAGAAAATG
TATTAATAGTATCTATGAATTTTCAGATGAAATTATATTTATT
GATACAGGATCAATTGATTCGACAAAAAAAATAGTAAAAGAAA
TAGCAAGCGAAAAGTAAAAATATTTGATTATACTTGGCAAGA
TGATTTTTCAGATGCGAGAAATTATTCAATACAAAAAGCAAGT
AAAGAATGGATATTAATTATTGATGCAGATGAATATGTATCTT
CAGATGAGCTTATCAAATTAAGGCTCTTAATAGATATGTTAGA
CAGGTTTAAATTTAAAGATTCATTAAGAGTTAGTTGTGCAATA
TATCAATTAGATAATGTTATCACACATGGCCAAAGTCGATTAT
TTAGAAACAATAATAAAATTAAGTATTATGGTCTAATACATGA
AGAGTTGAGGAACAACAAAGGATTAGATCCAATTTTTAACGTT
GAAAGTGAGATTACTTTTTTCCATGACGGTTACAAAGAAATAC
TTAGGAAAGAGAAGTGTGAAAGAAACATAAGGCTACTAGCTAA
GATGTTAGAAAAAGAGCCAGACAATGTTAGATGGGCATACTTG
TATTGTAGAGATTCATTTTCTATAAATTCCAACATTGATTTTG |

TABLE 2-continued

| Name | Role | Sequence (N→C) |
|------|------|----------------|
|  |  | AAAAAATTCTACTTCCATTTTTAATAAAGAATATGGATGAAAG<br>TATATCATGTGAGAATATCCTACTTACAAACTATACTCATTTA<br>ATCCTATTTCTTATTACTAAGAAATATATAATTGATGGGAAAA<br>GCTCACTTGCAAGTAAATGTATAGAGGTGTTAGAAAAAATGCT<br>ACCTAACTCTTCTGATGTTACTTTTTACAAATTTTTAAATAAA<br>CAGCATAGTTTGTATGAACAACAATTTGAATTTTTAAAAGAAG<br>TAATTCAATTTAGAAAAAATAATGAATATGATCAATATAGCCA<br>AATAGGGTGTAATTTATTACACTATGATTTATTAATTTCAGGA<br>TTACTTTTTGATGTTAAGTCTTATGATTATTCATATCAATACT<br>TTTTAAAATTAGATTTAGCTAACTATTTTTCTGAATTAGAGAT<br>TCCTGATGAATACAAAATGTTAATAAATAAGTATCGGGAGAAT<br>GAATCAC |

Example 6

Identification of Optimum Donor Substrates 0.2 μM purified recombinant nucleotide dependent glycosyltransferase is incubated with 5 μM acceptor substrate (SEQ ID NO: 4) in presence of an NDP sugar such as UDP-glucose, UDP-galactose, UDP-GlcNAc, UDP-GalNAc and GDP-mannose, GDP-glucose, GDP-fucose and UDP-glucuronic acid (in varying concentrations ranging 50 μM, 100 μM, 250 μM and 500 μM) in a reaction buffer containing 20 mM HEPES, pH 7.5, 50 mM NaCl and 1 mM TCEP. The reaction is then incubated at 25° C. for 12 hours. The reactions are quenched with 5% TFA to pH 2. The samples are desalted and subjected to MS analysis.

Example 7

Identification of Critical Residues in Protein Sequence for Activity of Recombinant Nucleotide Dependent Glycosyltransferase Various mutations are introduced in recombinant nucleotide dependent glycosyltransferase (GT-CTH) using side directed mutagenesis (Quick change lightning Mutagenesis kit, Agilent) using GTpET28a plasmid as template. The sequence of mutants is verified through DNA sequencing. The mutated recombinant plasmids are transformed into *E. coli* Lemo21(DE3) and *E. coli* BL21(DE3) cells for expression. The over expression, purification and functional analysis of mutants of recombinant nucleotide dependent glycosyltransferase proteins are performed using the above mentioned methods. The list of mutants of recombinant nucleotide dependent glycosyltransferase, created in accordance with present invention identifies D102, R136, W147, D152, A153, D154 residues critical for activity of recombinant nucleotide dependent glycosyltransferase (GT-CTH). Replacement of these residues to alanine results into abolishment of the glycosyltransferase activity.

TABLE 3

| S. No | Mutant Name | Expression status | In vitro glycosyltransferase activity status |
|-------|-------------|-------------------|----------------------------------------------|
| 1. | GT-CTH C87A | Soluble | Active |
| 2. | GT-CTH E97A | Soluble | Active |
| 3. | GT-CTH D102A | Soluble | Inactive |
| 4. | GT-CTH D130A | Soluble | Active |
| 5. | GT-CTH D131A | Soluble | Active |
| 6. | GT-CTH F132A | Soluble | Active |
| 7. | GT-CTH D130A, D131A | Soluble | Inactive |
| 8. | GT-CTH D131A, F132D | Soluble | Inactive |
| 9. | GT-CTH R136A | Soluble | Inactive |
| 10. | GT-CTH W147A | Soluble | Inactive |
| 11. | GT-CTH D152A | Soluble | Inactive |
| 12. | GT-CTH A153R | Soluble | Inactive |
| 13. | GT-CTH D154A | Soluble | Inactive |
| 14. | GT-CTH Y241A | Soluble | Active |

Therefore, the present invention provides more sugar enriched product by constructing a disaccharide and not just a monosaccharide glycan at one of three chemo-variant sites namely, serine or threonine or cysteine using single enzyme reaction. Furthermore, the invention is also capable of glyco-diversification thereby synthesizing at least four different disaccharide glycans and two different monosaccharide glycans on to the acceptor by using nucleotide dependent recombinant glycosyltransferase. Besides, the present invention is also useful to glycosylate and generates diversified glycoforms of bacteriocin like peptides or a polypeptide that harbor at least one exogenous or endogenous copy of minimal sequon corresponding to SEQ ID NO: 17 and variants thereof.

Hence, the present invention provides components to carry out glycosylation in vivo in a suitable prokaryotic host, which is useful for generating glycosylation in acceptor substrates where acceptor sites are not surface accessible in vitro. Furthermore, the present invention also provides method/components to carry out glycosylation in a cell free in vitro environment using appropriate reagents thereby creating useful/important neo-glycopeptides and or neo-bacteriocins.

Advantages of the Invention

This invention provides for one pot synthesis of a disaccharide glycan on to serine or threonine or cysteine residue in acceptor substrate.

This invention provides for creation of thioether linkages (S-linkage) between glycan and acceptor which are more useful, robust than ether linkages.

This invention provides for more sugar enriched product by constructing a disaccharide and not just a monosaccharide glycan at a single site using single enzyme reaction, wherein a disaccharide glycan or diglycan imparts better bioactivity than a monosaccharide glycan or mono-glycan in a glycosylated peptide like enterocin 96 peptide. However, the effect of glycan is not limited to influencing the bioactivity only.

Invention is capable of glyco-diversification and can synthesize at least four different disaccharide glycans and two monosaccharides on to the three different accepting residues namely, serine or threonine or cysteine in acceptor substrate, wherein nature and size of attached glycan affects the bioactivity of the glycosylated product but not limited to influencing bioactivity only.

This invention can be used to glycosylate and generate diversified glycoforms of bacteriocin like peptides that harbor at least one exogenous or endogenous copy of minimal sequon corresponding to SEQ ID NO: 17 and variants thereof.

This invention provides for useful components for directed evolution and for improvement of specificities of the invention described in.

The invention also provides components to develop a system to carry out glycosylation in vivo in a prokaryotic host and could be useful for generating glycosylation in acceptor substrate where acceptor sites are not surface accessible in vitro.

The present invention also provides method/components to carry out glycosylation in a cell free in vitro environment using appropriate reagents thereby creating useful/important neo-glycopeptides and neo-bacteriocins.

Other references (Main, P. J. (2014). Investigating the bacteriocin library *Lactobacillus plantarum* A-1. In Microbiology (Palmerston North, New Zealand, Massey University, Manuwatū Campus, Nant Kay Thwe Moe, S. M. T., Kousuke Suzuki, RyosukeNakai, Takeshi Terahara, Chiaki Imada, Takeshi Kobayashi (2015). Production of an antibacterial substance by *Bacillus mojavensis* strain F412 isolated from a Myanmar shrimp product fermented with boiled rice. Fisheries Science 81, 795-802, Tiwari, S. K., Sutyak Noll, K., Cavera, V. L., and Chikindas, M. L. (2015). Improved antimicrobial activities of synthetic-hybrid bacteriocins designed from enterocin E50-52 and pediocin PA-1. Appl Environ Microbiol 81, 1661-1667, Wang, Q., Zeng, X., Wang, S., Hou, C., Yang, F., Ma, X., Thacker, P., and Qiao, S. (2014). The bacteriocin sublancin attenuates intestinal injury in young mice infected with *Staphylococcus aureus*. Anatomical record (Hoboken, N.J.: 2007) 297, 1454-1461. EPO Patent No. CN102389030 B 12/2013 Li Ye A01N43/90, U.S. Pat. No. 5,641,668 A 6/1997 Eric G. Berger et al 435/193, U.S. Patent No. WO2000017226 A1 3/2000 Carolyn Bertozzi et al C12N5/02, U.S. Patent No. WO2008151258 A2 12/2008 Shawn Defrees et al G01N33/53, U.S. Pat. No. 8,895,014 B2 11/2014 Fabiana Fernandez et al 424/183.1, E.P. Patent No. WO2011073438 A3 7/2012 Roxanne Gavillon et al A61K8/64, Patent No. WO2002000851 A2 1/2002 Koji Hiratsuka et al C12N9/10, U.S. Patent No. WO2013088194 A1 6/2013 Sylviane Muller et al A61K38/04, U.S. Patent No. US20140033369 A11/2014 Yoshikazu Tanak et al 800/298, U.S. Pat. No. 8,257,949 B2 9/2012 Warren Wakarchuk et al 435/84, U.S. Pat. No. 6,743,606 B1 6/2004 Frank P. Wolter et al 435/97.

We claim:

1. An in vitro one pot method for synthesis of O-linked and/or S-linked diglycosylated products, the method comprising:
   (a) providing a mixture of a donor substrate and an acceptor substrate in a ratio in the range of 20:1 to 400:1, wherein the donor substrate comprises molecules of an activated nucleotide sugar selected from the group consisting of saccharide-UDP, and saccharide-GDP, and the acceptor substrate comprises a peptide or polypeptide having amino acid sequence selected from the group consisting of SEQ ID NO.: 4, SEQ ID NO.: 5, SEQ ID NO.: 6, SEQ ID NO.: 7, SEQ ID NO.: 8, SEQ ID NO.: 9, SEQ ID NO.: 10, SEQ ID NO.: 11, SEQ ID NO.: 12, SEQ ID NO.: 13, SEQ ID NO.: 14, SEQ ID NO.: 15, SEQ ID NO.: 16 and SEQ ID NO.: 17;
   (b) providing a multifunctional recombinant nucleotide dependent diglycosyltransferase protein having amino acid sequence selected from the group consisting of SEQ ID NO.: 1, SEQ ID NO.: 2, and SEQ ID NO.: 3;
   (c) contacting the multifunctional recombinant nucleotide dependent diglycosyltransferase protein of (b) with the mixture provided in (a); and
   (d) reacting the donor substrate and the acceptor substrate in presence of the multifunctional recombinant nucleotide dependent diglycosyltransferase protein, wherein the glycosyltransferase protein catalyzes the transfer of a saccharide moiety from the donor substrate to serine, threonine or cysteine residue in the acceptor substrate to obtain the O-linked and/or S-linked di-glycosylated products.

2. The method of claim 1, wherein the donor substrate saccharide-UDP sugar in step (a) is UDP-glucose or UDP-galactose and the GDP sugar is GDPglucose or GDP-galactose.

3. The method of claim 1, wherein the acceptor substrate in (a} comprising the peptide or the polypeptide comprises at least one exogenous or endogenous copy of amino acid sequence corresponding to minimal acceptor sequence of SEQ ID NO.: 17 and variants thereof.

4. The method of claim 1, wherein the di-glycosylated product is an antimicrobial peptide.

5. The method of claim 4, wherein the antimicrobial peptide is selected from enterocin 96 and glyco-variants thereof.

6. The method of claim 1, wherein the ratio of the donor substrate and the acceptor substrate is 20:1.

7. The method of claim 6, further comprising producing a mixture of glyco-diversified products using the di-glycosylated product to obtain a mixture of glycodiversified products, wherein the mixture comprises mono-glycosylated and diglycosylated products.

8. The method of claim 1, further comprising incubating the di-glycosylated product of (d) with an exoglycosidase that catalyzes removal of terminal saccharide moieties from the di-glycosylated products to obtain mono-glycosylated products.

9. The method of claim 8, wherein the exoglycosidase is selected from β-glucosidase and β-galactosidase.

10. The method of claim 1, further comprising separating and purifying the un-modified, mono-glycosylated and di-glycosylated product using RP-HPLC.

11. The method of claim 6, further comprising separating and purifying the un-modified, mono-glycosylated and di-glycosylated product using RP-HPLC.

12. The method of claim 8, further comprising separating and purifying the un-modified, mono-glycosylated and di-glycosylated product using RP-HPLC.

* * * * *